(12) United States Patent
Bae et al.

(10) Patent No.: US 7,209,775 B2
(45) Date of Patent: Apr. 24, 2007

(54) EAR TYPE APPARATUS FOR MEASURING A BIO SIGNAL AND MEASURING METHOD THEREFOR

(75) Inventors: Sang-kon Bae, Seoul (KR); Gil-won Yoon, Seoul (KR); Jong-youn Lee, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 298 days.

(21) Appl. No.: 10/824,387

(22) Filed: Apr. 15, 2004

(65) Prior Publication Data

US 2004/0225207 A1    Nov. 11, 2004

(30) Foreign Application Priority Data

May 9, 2003    (KR)    ............ 10-2003-0029365

(51) Int. Cl.
*A61B 5/00* (2006.01)
*A61B 5/02* (2006.01)
*A61B 5/08* (2006.01)

(52) U.S. Cl. ............... 600/340; 600/323; 600/324; 600/502; 600/529

(58) Field of Classification Search ........... 600/322, 600/323, 324, 340, 379
See application file for complete search history.

(56) References Cited

U.S. PATENT DOCUMENTS

| | | | |
|---|---|---|---|
| 5,002,060 A * | 3/1991 | Nedivi | 600/484 |
| 5,673,692 A | 10/1997 | Schulze et al. | |
| 6,078,829 A * | 6/2000 | Uchida et al. | 600/310 |
| 6,080,110 A | 6/2000 | Thorgersen | |
| 6,109,782 A | 8/2000 | Fukura et al. | |
| 6,361,501 B1 | 3/2002 | Amano et al. | |
| 6,371,925 B1 | 4/2002 | Imai et al. | |
| 6,396,416 B1 | 5/2002 | Kuusela et al. | |
| 6,454,705 B1 * | 9/2002 | Cosentino et al. | 600/300 |
| 6,816,741 B2 * | 11/2004 | Diab | 600/324 |
| 2002/0029000 A1 | 3/2002 | Ohsaki et al. | |
| 2002/0042558 A1 * | 4/2002 | Mendelson | 600/323 |
| 2003/0036685 A1 | 2/2003 | Goodman | |
| 2003/0163054 A1 * | 8/2003 | Dekker | 600/502 |

FOREIGN PATENT DOCUMENTS

CN    1 206 461    1/1999

(Continued)

OTHER PUBLICATIONS

Medical Science Series, Design of Pulse Oximeters,, Webster, J.G., Editor, pp. 40-55,.

*Primary Examiner*—Eric Winakur
*Assistant Examiner*—Etsub Berhanu
(74) *Attorney, Agent, or Firm*—Lee & Morse, P.C.

(57) ABSTRACT

An apparatus for measuring a bio signal including a bio signal measurement unit, which is insertable into an ear to be in close contact with an internal surface of the ear, the bio signal measurement unit having a photo plethysmography (PPG) measurement module for radiating light of different wavelengths onto the internal surface of the ear, detecting light transmitted through the ear, and outputting a PPG signal including bio information, a control unit having a PPG signal processor for generating the bio information using the PPG signal measured by the PPG measurement module, and an output unit for displaying the bio information generated from the control unit.

49 Claims, 14 Drawing Sheets

FOREIGN PATENT DOCUMENTS

| | | |
|---|---|---|
| EP | 0 770 349 | 5/1997 |
| JP | 5-504084 | 7/1993 |
| JP | 06-233745 | 8/1994 |
| JP | 9-122083 | 5/1997 |
| JP | 10-033511 | 2/1998 |
| JP | 63-84520 | 4/1998 |
| JP | 11-56827 | 3/1999 |
| JP | 11-178803 | 7/1999 |
| JP | 11-511301 | 9/1999 |
| JP | 2001-344678 | 12/2001 |
| JP | 2002-027051 | 1/2002 |
| JP | 2002-078690 | 3/2002 |
| JP | 2002-224050 | 8/2002 |
| KR | 10-353380 | 11/2000 |
| KR | 10/2002-0011730 | 2/2002 |
| WO | WO 91/11956 | 8/1991 |
| WO | WO 96/23442 | 8/1996 |
| WO | WO 96/41498 | 12/1996 |

\* cited by examiner

PPG SIGNAL

RESPIRATION SIGNAL

BAND-PASS FILTERED PPG

EAR TYPE APPARATUS FOR MEASURING A BIO SIGNAL AND MEASURING METHOD THEREFOR

BACKGROUND OF THE INVENTION

1. Field of the Invention

The present invention relates to an ear type apparatus for measuring a bio signal and a measuring method therefor. More particularly, the present invention relates to an ear type apparatus for measuring a bio signal, such as temperature, respiration, pulse, and oxygen saturation, which can minimize a motion artifact caused by a subject's motion, and a measuring method therefor.

2. Description of the Related Art

When a human body is in an abnormal state, various changes may occur such as an increase in blood pressure, an increase in pulse rate, an increase in body temperature, or a change in an electric potential occurring during a heartbeat, which may be measured by an electrocardiogram. Among these changes, the increase in body temperature is the most representative sign of an abnormal state of a human body and is thus generally measured during a patient diagnosis in hospitals or general medical institutions. Conventionally, body temperature is measured using a mercury thermometer. Recently, various ear type thermometers for measuring a body temperature, i.e., inner body temperature without influence from external temperature, have been developed. In operation, such an ear type thermometer detects an amount of infrared rays emitted from an eardrum at an internal body temperature and converts the detected amount of infrared rays into a temperature value. The ear type thermometer is advantageous in that a measurement time is short and the body temperature can be conveniently measured by inserting the ear type thermometer into an ear.

A pulse indicates a dynamic extension of an artery that can be felt by a finger. Since the dynamic extension of an artery is due to a contraction of the heart, a heart rate, i.e., a heart's contraction rate, can be inferred from a pulse rate. When a human body is infected by a disease, the pulse rate, rhythm, or strength changes even when the human body is in a stable status. Accordingly, a person's state of health can be checked by measuring the pulse rate, rhythm, or strength.

Further, oxygen saturation indicates an amount of arterial blood ($SpO_2$) in which oxygen is saturated. Oxygen saturation is measured to test a pulmonary function, estimate a concentration of oxygen in blood during oxygen therapy at home, or diagnose asthma and pulmonary emphysema. Human respiration is a process of discharging waste gas, i.e., carbonic acid gas, from a human body and providing oxygen to the human body. A human lung accommodates air coming from outside, emits carbonic acid gas, and absorbs oxygen. A pulmonary artery discharges carbonic acid gas collected throughout the human body through pulmonary alveoli using a difference in air pressure during exhalation. Conversely, blood in a pulmonary vein absorbs oxygen from inhaled air and then circulates to the heart. When respiration is unstable, a supply of oxygen is interrupted, which deteriorates the functions of a body's organs. In particular, oxygen saturation directly relates to an amount of oxygen supplied to the organs and thus provides very useful information regarding metabolism.

FIG. 1 shows an example of a conventional ear type thermometer for measuring body temperature. The ear type thermometer shown in FIG. 1 includes a housing 150 having a probe 110 through which infrared rays pass, a light receiver 120 that receives infrared rays emitted from at least one area from among a human eardrum and peripheral areas of the eardrum through the probe 110, a signal processor 130 that calculates a temperature from an output of the light receiver 120, and a display/sound unit 140 that displays the temperature.

The light receiver 120 includes a condenser device, which condenses infrared rays passing through the probe 110, and an infrared receiver device, which is disposed to receive the infrared rays condensed by the condenser device to receive infrared rays emitted from at least one area from among the eardrum and the peripheral areas of the eardrum.

Disadvantageously, the conventional ear type thermometer shown in FIG. 1 is a separate device that has to be additionally carried by a user. Moreover, a tip of the probe 110 of the thermometer needs to be in close contact with an internal surface of a subject's ear in order to accurately measure the subject's body temperature. However, when another person measures a subject's body temperature, the contact between the thermometer and the internal surface of the ear cannot be adjusted effectively. Although the subject can directly adjust the contact when measuring his own body temperature, the subject must remove the thermometer from the ear to view the display unit to check a measured value and verify whether the measurement has been accurately performed. Accordingly, this thermometer is not appropriate for self-diagnosis and is thus usually used when another person measures a subject's body temperature.

In order to apply such a conventional ear type thermometer to a remote medical treatment, since a measured value needs to be transmitted via a separate transmission apparatus, an interface is required. Accordingly, it is difficult to monitor results of the measurement frequently or for an extended period of time.

FIG. 2 shows an example of a conventional mobile apparatus that is capable of measuring a bio signal. The exemplary mobile apparatus shown in FIG. 2 is a portable communication terminal, which allows a function of a heart to be diagnosed or obesity to be tested based on a heart rate and a body fat rate, which are detected from a user's body. This apparatus eliminates an inconvenience of carrying a separate apparatus solely for measuring bio information. Electrodes 2a, 2b, 2c, and 2d are attached to an outer surface of a mobile communication terminal in order to measure a user's bio information.

FIG. 3 is a block diagram of the conventional mobile apparatus shown in FIG. 2. A portable communication terminal 300 includes a communication terminal module 320 and a bio-information measurement module 310 to provide dual functionality of voice communication and bio information measurement. The communication terminal module 320 includes a transceiver 326 as a user interface unit, a display unit 321, such as a liquid crystal display (LCD), allowing communication of character information, and an input unit 322 such as a keypad. The input unit 322 is used by a user to operate or control the portable communication terminal 300. Communication of information can be implemented by wireless transmission and reception of data via a wireless communication unit 323. A memory unit 324 stores information regarding the user of the portable communication terminal 300 and data necessary for the operation of the central controller 325.

The bio-information measurement module 310 includes a body fat measurer 311 and a heart rate measurer 312. An interface unit 313 performs data interface between the portable communication terminal 300 and an external electronic apparatus, for example, a removable bio-information measurement module.

FIG. 4 is a detailed block diagram of the heart rate measurer 312. The heart rate measurer 312 includes a voltage generator 401, electrodes 402, an amplifier 403, a pulse shaper 404, a pulse counter 405, and an interface unit 406. When the electrodes 402 of the voltage generator 401, which are attached to a main body of the portable communication terminal 300, are in close contact with a part of a subject's body, for example, right and left hands, a voltage change signal due to the heart's beat is detected. The voltage change signal is amplified by the amplifier 403, for example, a differential amplifier. The amplified voltage change signal is converted to a pulse signal by the pulse shaper 404. The pulse signal is counted by the pulse counter 405 to obtain a heart rate. An output signal of the pulse counter 405 is a digital signal and is input to the interface unit 406. The central controller (325 of FIG. 3) displays the heart rate on the display unit 321 and transmits it through the wireless communication unit 323. Voltage measurement electrodes used to measure body fat in the body fat measurer 311 are also used as the electrodes 402.

Disadvantageously, such a conventional portable communication terminal for measuring bio information using electrodes is influenced by a motion artifact caused by a force pressing the electrodes and is sensitive to contamination of the electrodes or the skin since the electrodes directly contact the skin. When the electrodes are exposed outside the communication terminal, they are easily damaged or contaminated.

To obtain bio information, such as oxygen saturation, a component in blood needs to be detected. Accordingly, a method of applying signals showing different characteristics according to concentrations of oxidized hemoglobin and reduced hemoglobin and obtaining the bio information using a difference between the signals is usually used. In conventional methods, however, since one electrode cannot apply different types of signals, bio information beyond a pulse rate cannot be appropriately measured.

SUMMARY OF THE INVENTION

The present invention provides an apparatus for measuring a bio signal, which is convenient to carry, can be adjusted to be correctly positioned at a body part to be measured by a subject himself, and can transmit measured bio information without requiring a separate transmitter, thereby facilitating long-term monitoring. In addition, the apparatus can obtain pulse and respiration information and simultaneously measure oxygen saturation using changes in absorptance of light having at least two different wavelengths. The present invention further provides a method for measuring a bio signal.

According to a feature of an embodiment of the present invention, there is provided an apparatus for measuring a bio signal including a bio signal measurement unit, which is insertable into an ear to be in close contact with an internal surface of the ear, the bio signal measurement unit having a photo plethysmography (PPG) measurement module for radiating light of different wavelengths onto the internal surface of the ear, detecting light transmitted through the ear, and outputting a PPG signal including bio information, a control unit having a PPG signal processor for generating the bio information using the PPG signal measured by the PPG measurement module, and an output unit for displaying the bio information generated from the control unit.

According to another feature of an embodiment of the present invention, there is provided an apparatus for measuring a bio signal including a bio signal measurement unit, which is insertable into an ear to be in close contact with an internal surface of the ear, the bio signal measurement unit having a photo plethysmography (PPG) measurement module for radiating light of different wavelengths onto the internal surface of the ear, detecting light transmitted through the ear, and outputting a PPG signal including bio information, and further having a plurality of electrodes for outputting the PPG signal, an earphone having a speaker for outputting sound and a plurality of electrodes on an outer surface to be connected to the plurality of electrodes of the bio signal measurement unit to receive the PPG signal output from the bio signal measurement unit, a control unit having a PPG signal processor for receiving the PPG signal through the electrodes of the earphone and generating bio information using the PPG signal and a sound processor for outputting a sound signal to the earphone, and an output unit for displaying the bio information generated from the control unit.

Preferably, the PPG measurement module includes a light source unit for radiating light onto the internal surface of the ear and a photodetector for detecting light radiated onto the internal surface of the ear and then transmitted through the ear. The light source unit may include a first light source for radiating light of a first wavelength onto the internal surface of the ear, and a second light source for radiating light of a second wavelength onto the internal surface of the ear, wherein the first and second wavelengths are different.

Preferably, the PPG signal processor includes a peak detector for detecting peaks of the PPG signal and a signal processor for generating the bio information using values of the peaks. The signal processor may include a pulse detector for calculating a time interval between the peaks to measure a pulse rate. The signal processor may include a respiration detector for band-pass filtering the PPG signal to measure a respiration frequency. The signal processor may include a reflection coefficient detector for detecting an AC component and a DC component from each of PPG signals detected at different wavelengths and measuring reflection coefficients and an oxygen saturation detector for detecting oxygen saturation in blood using a ratio between the reflection coefficients of the different wavelengths.

The PPG signal processor may further include an amplifier for amplifying the PPG signal and a filter for removing noise components from the PPG signal amplified by the amplifier and then outputting the PPG signal to the peak detector.

Preferably, the bio signal measurement unit further includes a temperature measurement module for sensing infrared rays radiated from a body and outputting an electrical signal corresponding to the sensed infrared rays, and wherein the control unit further includes a temperature processor for calculating a body temperature using the electrical signal output from the temperature measurement module. The temperature measurement module may include a waveguide installed near an eardrum for guiding infrared rays radiated from the eardrum and a light receiver sensing the infrared rays guided by the waveguide and converting the infrared rays to the electrical signal. The waveguide may be made of a material that can reflect infrared rays. The temperature processor may include an amplifier for amplifying the electrical signal received from the temperature measurement module, a filter for removing noise from the amplified electrical signal, and an analog-to-digital converter for converting the electrical signal to a digital signal.

The output unit may be a liquid crystal display apparatus. Further, the output unit may be a liquid crystal display apparatus of a mobile communication terminal or a compact disc player.

The bio information unit may further include a mobile communication terminal through which the bio information generated from the control unit is wirelessly transmitted to a predetermined medical institution.

According to still another feature of an embodiment of the present invention, there is provided a method of measuring a bio signal using an ear type bio signal measurement apparatus including a bio signal measurement unit, which is insertable into an ear to measure a bio signal, a control unit for generating bio information using the measured bio signal, and an output unit for outputting the bio information, the method including (a) receiving infrared rays radiated from an eardrum and measuring a body temperature using the bio signal measurement unit, (b) radiating light having different wavelengths onto an internal surface of an ear, which is in close contact with the bio signal measurement unit, to measure a photo plethysmography (PPG) signal including bio information and measuring at least one bio signal from among the group consisting of oxygen saturation, a pulse rate, and a respiration frequency, using the PPG signal, and (c) outputting the at least one bio signal measured in (a) and (b), wherein (a) and (b) are simultaneously performed.

Preferably, (b) includes (b1) radiating the light having the different wavelengths onto the internal surface of the ear, receiving the light transmitted through the ear, and outputting the PPG signal, using a PPG measurement module included in the bio signal measurement unit having a side thereof in close contact with the internal surface of the ear; (b2) detecting peaks of the PPG signal; and (b3) generating bio information using the detected peaks.

Preferably, (b3) includes detecting an AC component and a DC component from each of PPG signals detected at the different wavelengths and measuring reflection coefficients of the different wavelengths, and calculating oxygen saturation in blood using a ratio between the reflection coefficients of the different wavelengths. Preferably, (b3) includes band-pass filtering the PPG signal to detect a respiration frequency. In addition, (b2) may include band-pass filtering the PPG signal collected for a predetermined period of time, detecting an inflection point by differentiating the filtered PPG signal, and storing the inflection point as a peak when the inflection point has a value exceeding a predetermined threshold value.

Preferably, (b3) may include measuring a pulse rate using a time interval between peaks of the PPG signal. The output unit may be a liquid crystal display apparatus of a mobile communication terminal, and (c) may further include wirelessly transmitting the bio signals measured in (a) and (b) to a predetermined medical institution through the mobile communication terminal.

According to yet another feature of an embodiment of the present invention, there is provided a recording medium having recorded therein a program for executing the above-described method in a computer.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE INVENTION

Figure 1:
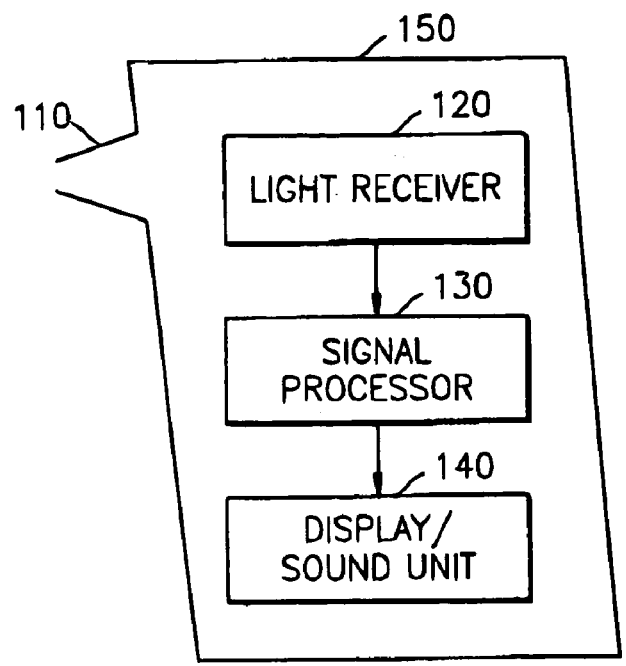
FIG. 1 shows an example of a conventional ear type thermometer for measuring body temperature.
Figure 2:
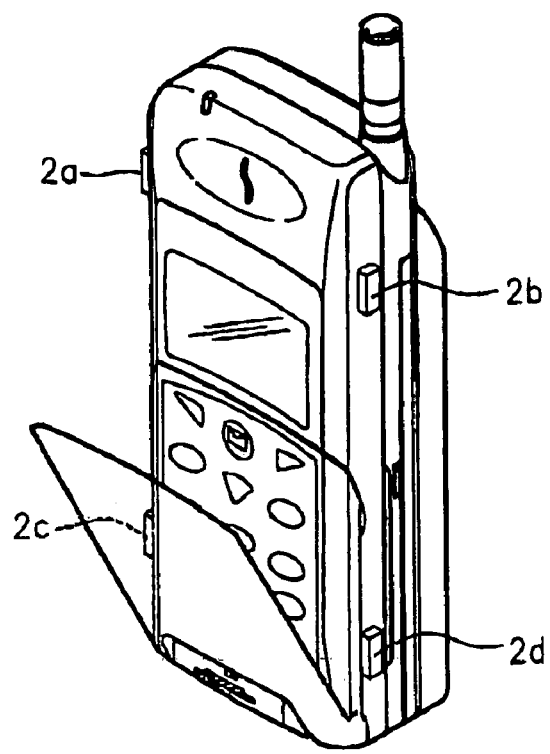
FIG. 2 shows an example of a conventional mobile apparatus that is capable of measuring a bio signal.
Figure 3:
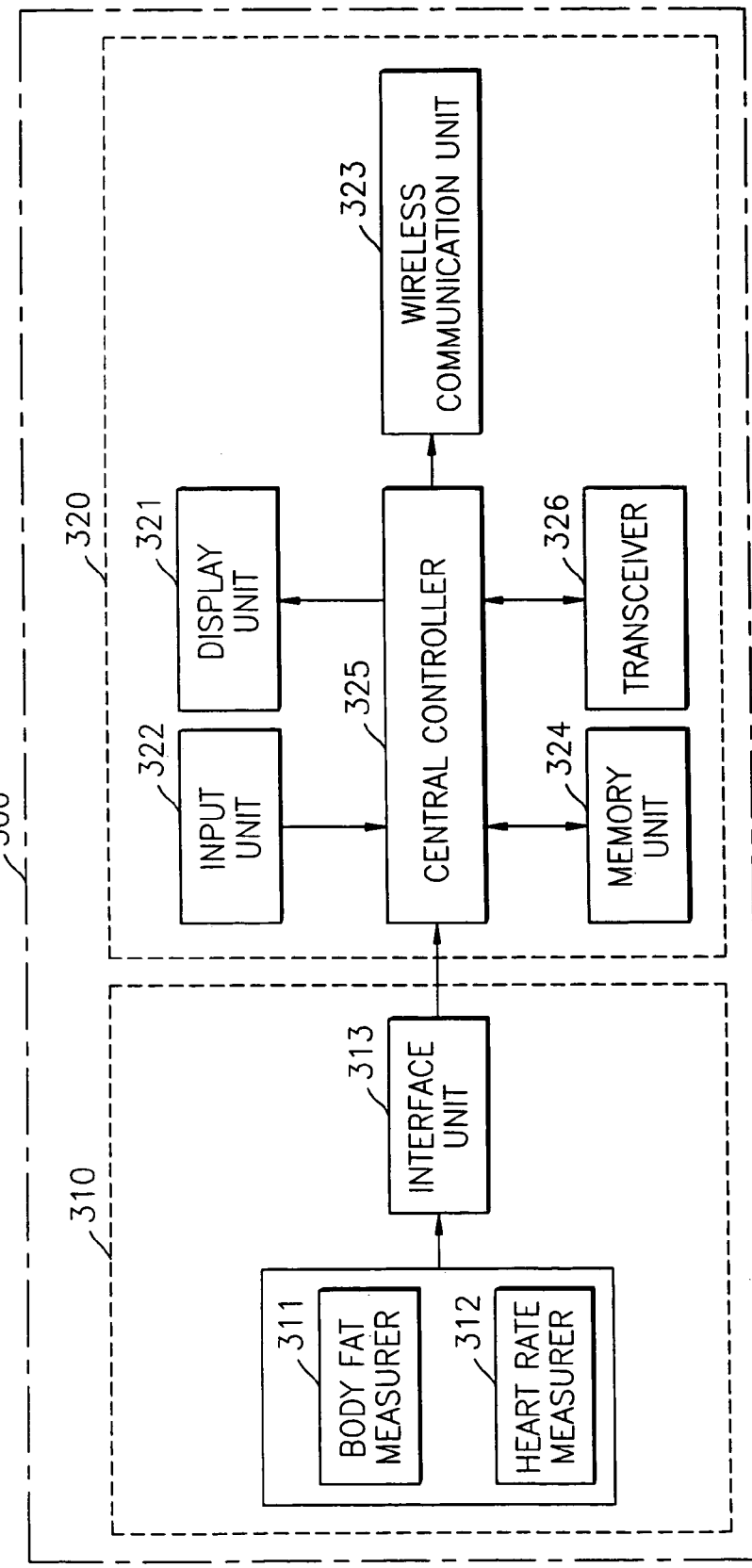
FIG. 3 is a block diagram of a conventional mobile apparatus as shown in FIG. 2.
Figure 4:
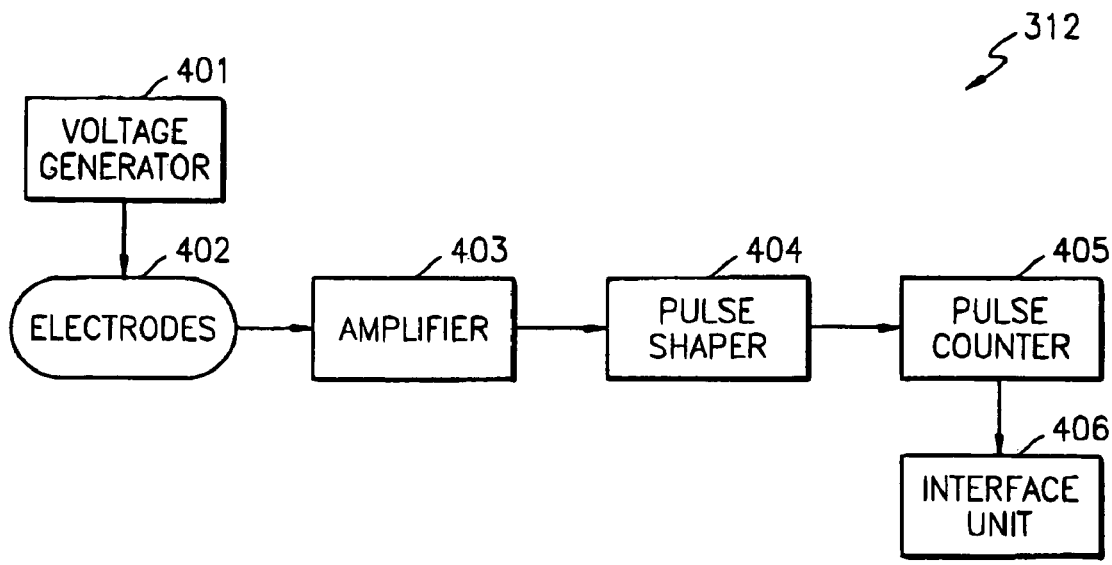
FIG. 4 is a detailed block diagram of a conventional heart rate measurer as shown in FIG. 3.

Korean Patent Application No. 2003-29365, filed on May 9, 2003, and entitled: "Ear Type Apparatus for Measuring a Bio Signal and Measuring Method Therefor," is incorporated by reference herein in its entirety.

The present invention will now be described more fully hereinafter with reference to the accompanying drawings, in which preferred embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

Figure 5A:
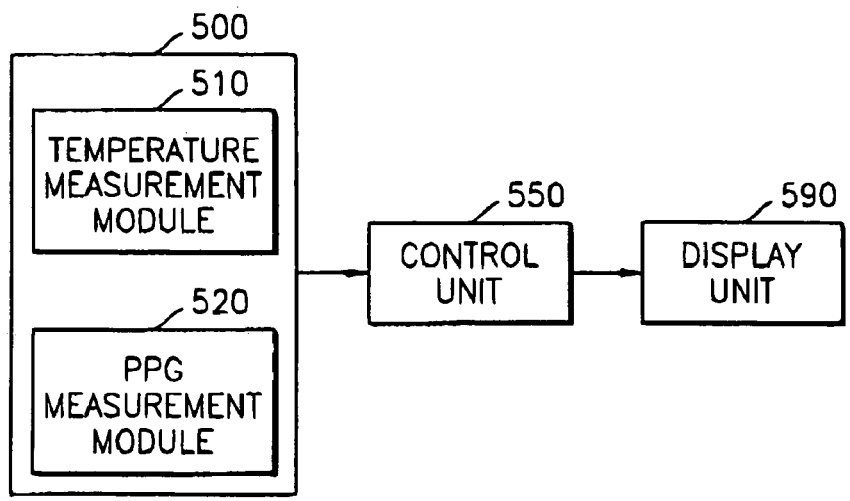
FIG. 5A is block diagram of an apparatus for measuring a bio signal according to a first embodiment of the present invention.
Figure 5B:
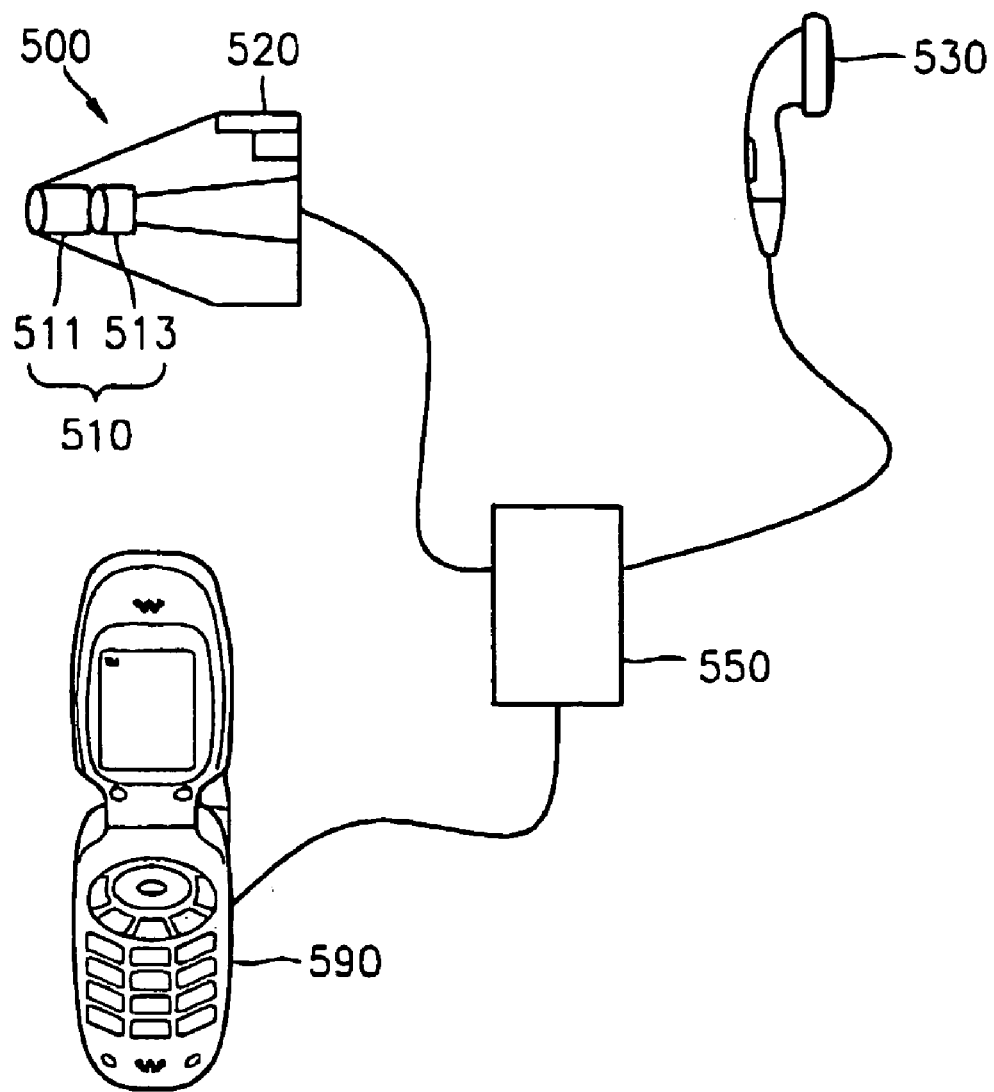
FIG. 5B shows an example in which an apparatus for measuring a bio signal according to an embodiment of the present invention is applied to a mobile apparatus.

FIG. 5A is block diagram of an apparatus for measuring a bio signal according to a first embodiment of the present invention. FIG. 5B shows an example in which an apparatus for measuring a bio signal according to the first embodiment of the present invention is applied to a mobile apparatus.

Referring to FIG. 5A, the apparatus according to the first embodiment of the present invention includes a bio signal measurement unit 500, which is insertable into an ear to measure a bio signal; a control unit 550, which calculates bio information using the bio signal measured by the bio signal measurement unit 500; and a display unit 590, which displays the bio information on a screen for a user. The bio signal measurement unit 500 includes a temperature measurement module 510, which measures body temperature using infrared rays radiated from an internal surface of an ear, and a photo plethysmography (PPG) measurement module 520, which is installed on an outer surface of the bio signal measurement unit 500 to closely contact the internal surface of the ear and measure a PPG signal.

Referring to FIGS. 5A and 5B, the bio signal measurement unit 500 can be easily inserted into the ear due to its shape. The PPG measurement module 520 is installed at the outer surface of the bio signal measurement unit 500 to closely contact the ear surface. The temperature measurement module 510 is installed in the bio signal measurement unit 500 at a position that will be in relatively close proximity to an eardrum. The bio signal measurement unit 500 may have a same shape as an earphone 530, as shown in FIG. 5B. However, since it is preferable that the temperature measurement module 510 is positioned near the eardrum so that it can effectively sense infrared rays radiated from the eardrum, it is preferable to shape the bio signal measurement unit 500 as a conical frustum and to dispose the temperature measurement module 510 at a top of the conical frustum-shaped bio signal measurement unit 500. The temperature measurement module 510 includes a waveguide 511 guiding infrared rays near the eardrum to the bio signal measurement unit 500 and a light receiver 513 implemented by an infrared sensor to sense the infrared rays input through the waveguide 511.

For the display unit 590, a separate display apparatus or a display apparatus included in an existing apparatus can be used. In the example shown in FIG. 5B, a mobile apparatus is used as the display unit 590. The display unit 590 may be implemented by a liquid crystal display (LCD) of a mobile communication terminal (as shown in FIG. 5B), a personal digital assistant (PDA), a compact disc player, or the like. When a mobile communication terminal is used, bio information can be transmitted to a predetermined medical institution, so that remote examination can be performed. Hereinafter, it is assumed that a mobile apparatus is used for the display unit 590.

In FIG. 5B, the control unit 550 is shown separate from the bio signal measurement unit 500. The control unit 550 calculates bio information using a signal received from the bio signal measurement unit 500 and outputs the bio information to the display unit 590. When a mobile apparatus is used for the display unit 590, the control unit 550 can be installed within the mobile apparatus. When the control unit 550 is separately installed outside the mobile apparatus, it can be provided with a jack, which can be connected to the earphone 530, as shown in FIG. 5B, so that the control unit 550 controls a sound signal output from the mobile apparatus and outputs the sound signal to the earphone 530.

Figure 6:
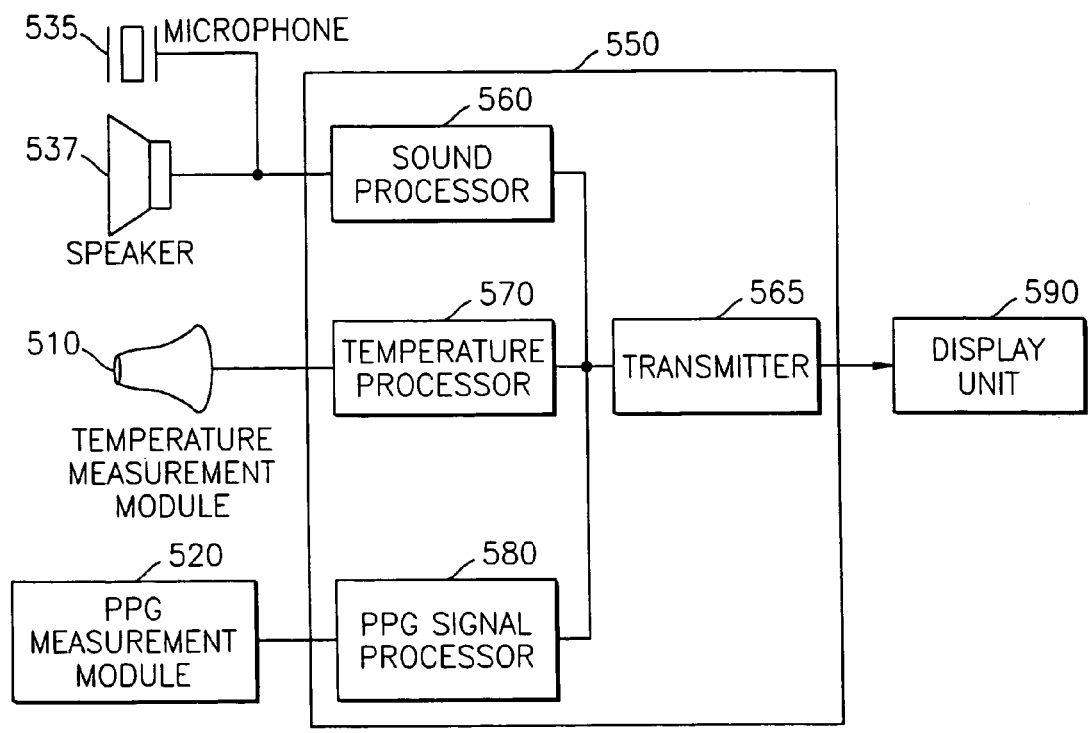
FIG. 6 is a block diagram showing a control unit as shown in FIG. 5A.

FIG. 6 is a block diagram showing the control unit 550 shown in FIG. 5A. The control unit 550 includes a temperature processor 570, which converts a signal detected by the infrared sensor of the temperature measurement module 510 to a temperature value; a PPG signal processor 580, which generates measurement values of a pulse rate, a respiration frequency, and oxygen saturation using the PPG signal measured by the PPG measurement module 520; and a transmitter 565, which selectively transmits an output signal from the temperature processor 570 and an output signal from the PPG signal processor 580 to the mobile apparatus according to a selection signal of the mobile apparatus used for the display unit 590. When the earphone 530, which can output a sound signal from the mobile apparatus, is connected to the control unit 550, the control unit 550 further includes a sound processor 560, which receives a voice signal through a microphone 535, outputs a voice signal from the mobile apparatus through a speaker 537, and adjusts the volume of the output voice signal. Meanwhile, it will be apparent that the signals of the sound processor 560, the temperature processor 570, and the PPG signal processor may be directly input to the mobile apparatus, and a control unit (not shown) included in the mobile apparatus including the display unit 590 may selectively output the signals.

Figure 7:
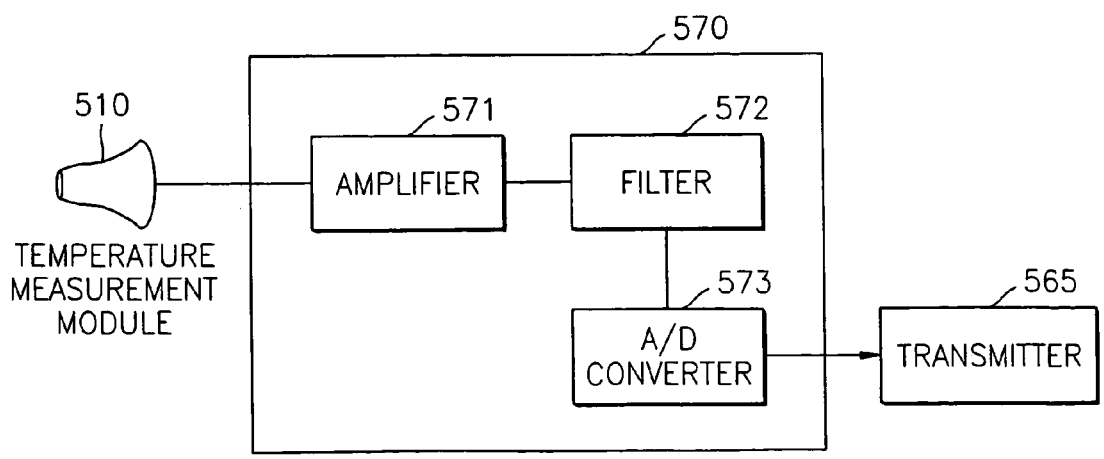
FIG. 7 is a detailed block diagram showing a temperature processor as shown in FIG. 6.

FIG. 7 is a detailed block diagram showing the temperature processor 570 shown in FIG. 6. The temperature processor 570 includes an amplifier 571, which amplifiers a signal output from the temperature measurement module 510; a filter 572, which removes noise components from the amplified signal; and an analog-to-digital (A/D) converter 573, which converts the filtered signal to a digital signal and transmits the digital signal to the transmitter 565.

Figure 8:
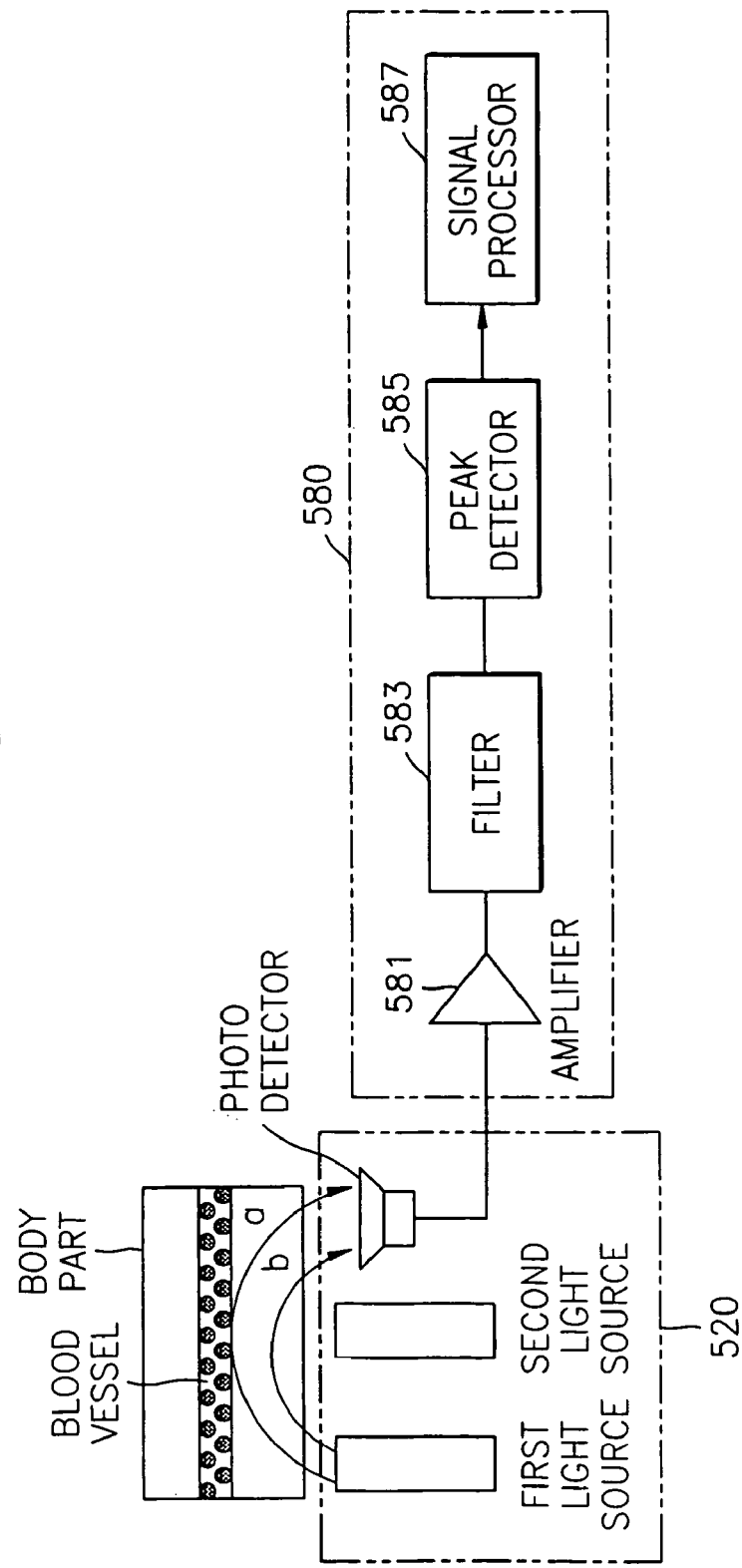
FIG. 8 is a detailed block diagram showing a photo plethysmography (PPG) measurement module and a PPG signal processor as shown in FIG. 6.

FIG. 8 is a detailed block diagram showing the PPG measurement module 520 and the PPG signal processor 580 shown in FIG. 6. The PPG measurement module 520 includes a first light source, which radiates light onto a body part, i.e., an internal surface of an ear closely contacting the bio signal measurement unit 500, at which a bio signal is to be measured; a second light source, which radiates light having a different wavelength than the light of the first light source onto the body part; and a photodetector, which detects light that has been radiated from the first and second light sources and then transmitted through and reflected from the body part with bio information. The PPG signal processor 580 includes an amplifier 581, which amplifies a signal output from the photodetector; a filter 583, which removes noise components from an output signal of the amplifier 581; a peak detector 585, which detects a peak from an output signal from the filter 583; and a signal processor 587, which calculates bio information using a peak value of a signal detected from the light from the first light source and a peak value of a signal detected from the light from the second light source and outputs the bio information to the display unit 590.

Figure 9:
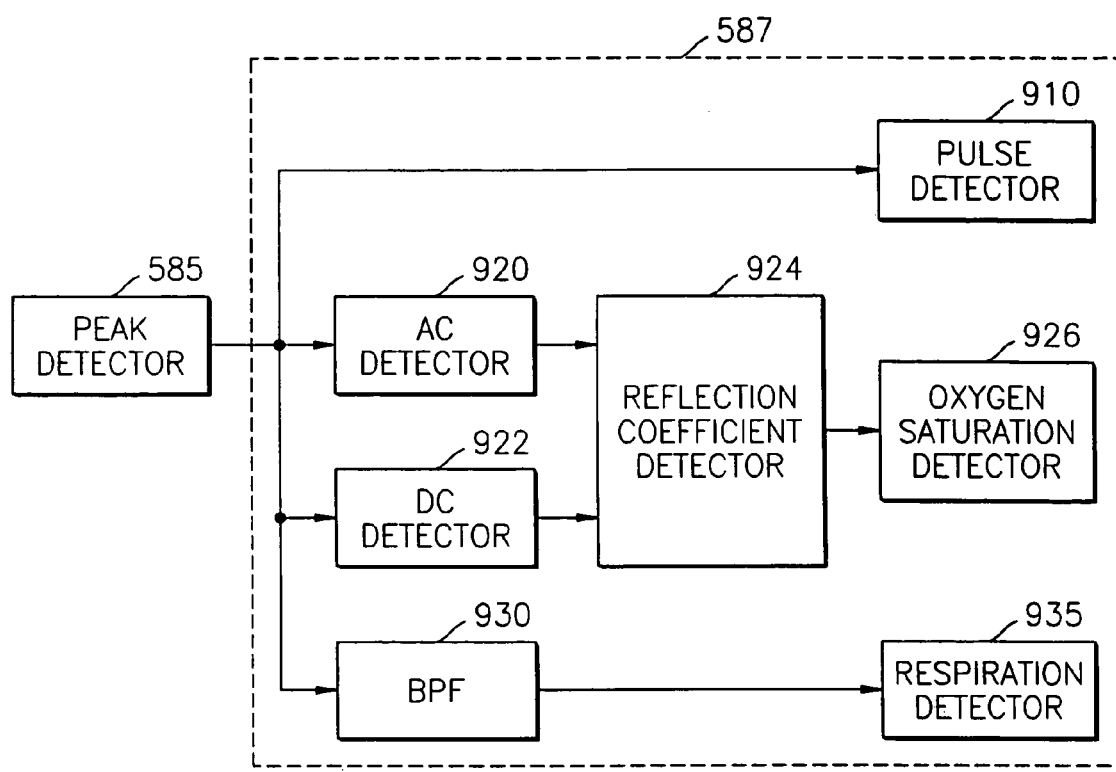
FIG. 9 is a detailed block diagram showing a signal processor as shown in FIG. 8.

FIG. 9 is a detailed block diagram showing the signal processor 587 shown in FIG. 8. In order to measure a subject's pulse, the signal processor 587 includes a pulse detector 910, which calculates a time interval between peaks detected by the peak detector 585 and measures a pulse based on the time interval.

In order to measure a subject's oxygen saturation, the signal processor 587 includes an alternating current (AC) detector 920, which detects changes between maximum values and minimum values of a waveform output from the peak detector 585 to detect a light intensity variation due to pulsatile components of an artery; a direct current (DC) detector 922, which detects the minimum values of the waveform output from the peak detector 585 to detect a light intensity due to non-pulsatile components; a reflection coefficient detector 924, which calculates a reflection coefficient using a DC component and an AC component of a pulse wave; and a oxygen saturation detector 926, which calculates oxygen saturation using the reflection coefficient.

In order to detect a subject's respiration frequency (rate), the signal processor 587 includes a band pass filter (BPF) 930, which band pass filters a pulse signal received from the peak detector 585, and a respiration detector 935, which detects a respiration frequency using the band pass filtered pulse signal.

Hereinafter, a method of measuring a bio signal according to an embodiment of the present invention will be described with reference to FIGS. 10 through 15B.

Initially, a method of measuring temperature using the bio signal measurement unit 500 will be described. Since a temperature of human skin tissue varies at different body parts and rapidly changes depending on external temperature, it is important to select an appropriate body part for temperature measurement. Generally, a contact type thermometer is used at an armpit or the rectum, and a non-contact type thermometer is used in an ear canal near an eardrum. The temperature of the eardrum is medically known as being very close to internal body temperature and barely influenced by external temperature. The internal body temperature and radiant electromagnetic energy or infrared energy are related as follows.

A total amount of electromagnetic energy radiated from a black body is proportional to the fourth power of the temperature of the black body according to Stefan-Boltzmann's Law, as shown in Formula (1).

$$Q=\sigma T^4 \tag{1}$$

Here, Q represents a total amount of electromagnetic energy radiated from the black body, T denotes the temperature of the black body, and σ denotes a constant called the Stefan-Boltzmann constant. An amount of electromagnetic energy radiated from a body, such as a human body, that is not completely black is influenced by radiant components of the body. Such a body is referred to as a gray body. When the emissivity of the gray body is ω, Formula (1) is modified into Formula (2).

$$Q=\omega\sigma T^4 \tag{2}$$

Here, the emissivity ω has a value between zero (0) and one (1). The emissivity ω of a human body in a far infrared band is almost one (1), exhibiting characteristics near to those of a black body. Accordingly, an absolute internal body temperature can be calculated using the total amount of infrared energy radiated from the internal body. In addition, a change in the infrared energy is proportional to the fourth power of a change in the internal body temperature.

Figure 10:
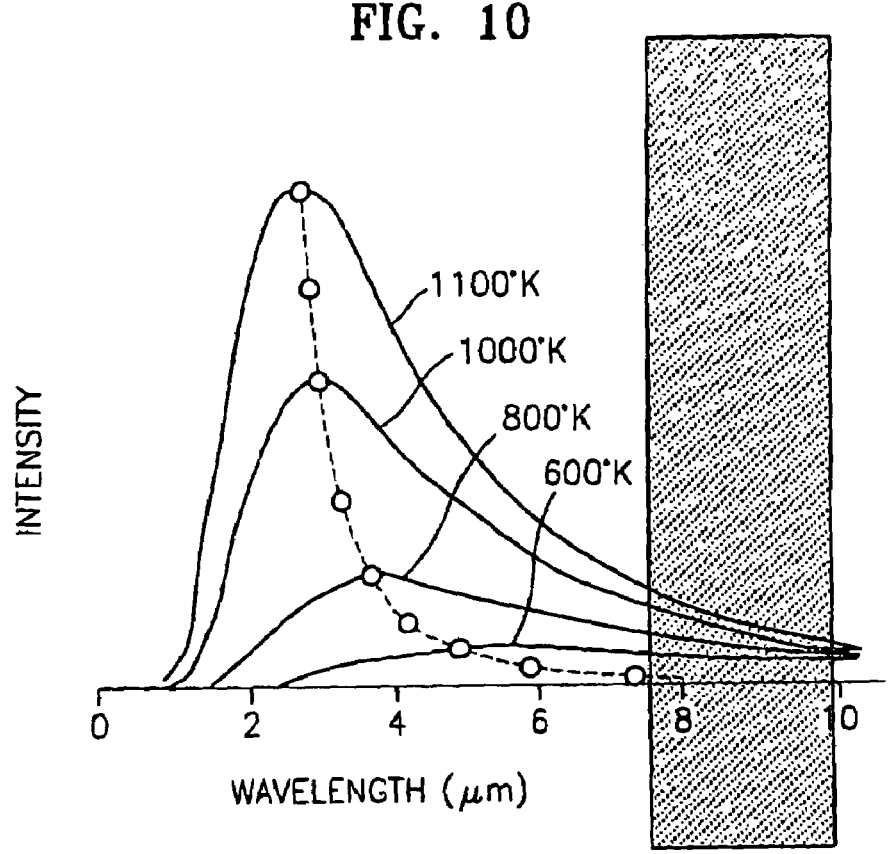
FIG. 10 is a graph of intensity of radiant energy of a black body versus wavelength.

FIG. 10 is a graph of an intensity of radiant energy versus wavelength at different temperatures of a black body. Energy radiated from the black body at a constant temperature gradually increases as the wavelength increases and reaches a peak. Thereafter, when the wavelength further increases, the radiant energy decreases. A peak of such a characteristic curve changes as temperature changes, and a wavelength at which the peak occurs also varies with the temperature. As shown in FIG. 10, when the temperature is 1100 K, a peak occurs at a wavelength of about 2.5 μm. When the temperature decreases to 800 K, a peak occurs at a wavelength of about 3.8 μm and the intensity of radiant energy decreases. A wavelength λ giving maximum radiant energy at a particular temperature T is defined by Formula (3).

$$\lambda(max)=0.29/T \tag{3}$$

Since targets of a non-contact type infrared thermometer generally have a temperature of about 30–40° C., the targets radiate far infrared rays in which a wavelength of about 8–12 μm provides maximum radiant energy. Accordingly, a photodetector for detecting the far infrared rays is required to have a satisfactory response characteristic in a band of about 8–12 μm.

Figure 11:
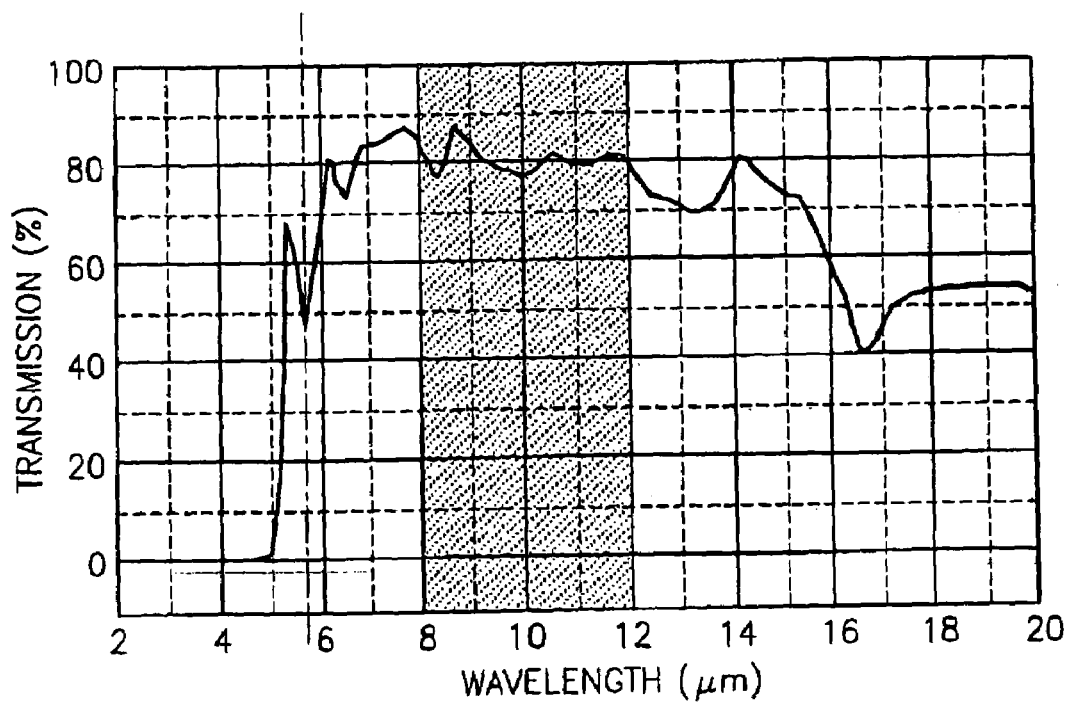
FIG. 11 is a graph showing a transmission characteristic of a sensor filter.
Figure 12:
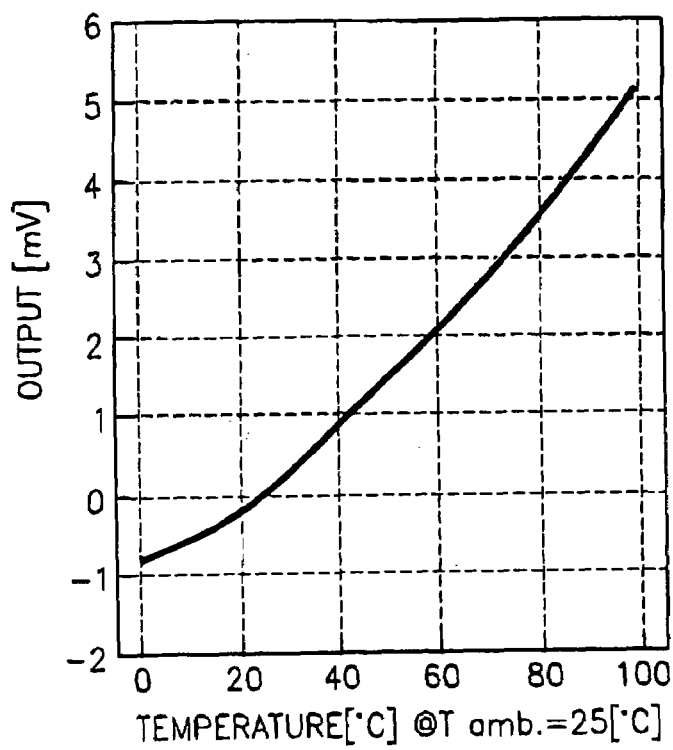
FIG. 12 is a graph showing a temperature characteristic of a sensor.

A filter of a general sensor used in infrared thermometers needs to have a frequency response characteristic as shown in FIG. 11. More specifically, it is preferable that a response is great at a wavelength of about 6–16 μm, but almost constant transmission appears at the band of about 8–12 μm. Though a total amount of electromagnetic energy radiated from the black body is proportional to the fourth power of the temperature of the black body, when a measurement range is very narrow, for example, 30–40° C., as in a thermometer, the total amount of electromagnetic energy can be considered as being linear within the range of 30–40° C. FIG. 12 is a graph of output voltage of the sensor used in FIG. 11 versus temperature. As described above, a linear characteristic appears in a temperature range of 30–40° C.

Based on the above-described response of an infrared sensor, the operating principle of the temperature measurement module 510 of the present invention will be described with reference to FIGS. 5B and 7. As described above, the temperature measurement module 510 includes the waveguide 511 for collecting light and the light receiver 513 implemented by an infrared sensor. The waveguide 511 is disposed near an eardrum to collect radiant infrared rays. The waveguide 511 includes a material reflecting infrared rays therewithin to guide the collected infrared rays to the light receiver 513. Then, the light receiver 513 installed within the bio signal measurement unit 500 detects the infrared rays and generates an electrical detection signal according to an amount of the infrared rays.

Since the electrical detection signal is too weak to be transmitted or digitized, the signal is amplified by the amplifier 571. The amplified detection signal includes a plurality of noise components, but a signal component required for measurement of body temperature is a DC component appearing in a peak wavelength rather than an AC component changing over time. Accordingly, the amplified detection signal is filtered by the filter 572 to remove the noise and AC components. The filtered detection signal is converted to a digital value by the A/D converter 573. The A/D converter 573 also converts the digital value to a temperature value to be displayed to a user.

However, when the display unit 590 is implemented by an LCD included in a mobile apparatus, such as a mobile communication terminal as shown in FIG. 5B, the A/D converter 573 simply converts an analog signal to a digital signal. The digital signal can be converted to a temperature value by an operation unit included in the mobile apparatus and then output to the user through the display unit 590. In addition, it is obvious to those skilled in the art that the control unit 550 including the temperature processor 570 can be installed within the mobile apparatus including the display unit 590 so that the temperature measurement module 510 may be directly connected to the mobile apparatus.

When a user measures his own body temperature using a thermometer provided in the ear type bio signal measurement unit 500, the user inserts the bio signal measurement unit 500 into his ear and monitors the display unit 590. Thus, the user himself can take a measurement and check the results of the measurement. In addition, when re-measurement is required since the bio signal measurement unit 500 is not appropriately inserted into the ear, the user himself can adjust the insertion of the bio signal measurement unit 500.

Figure 13:
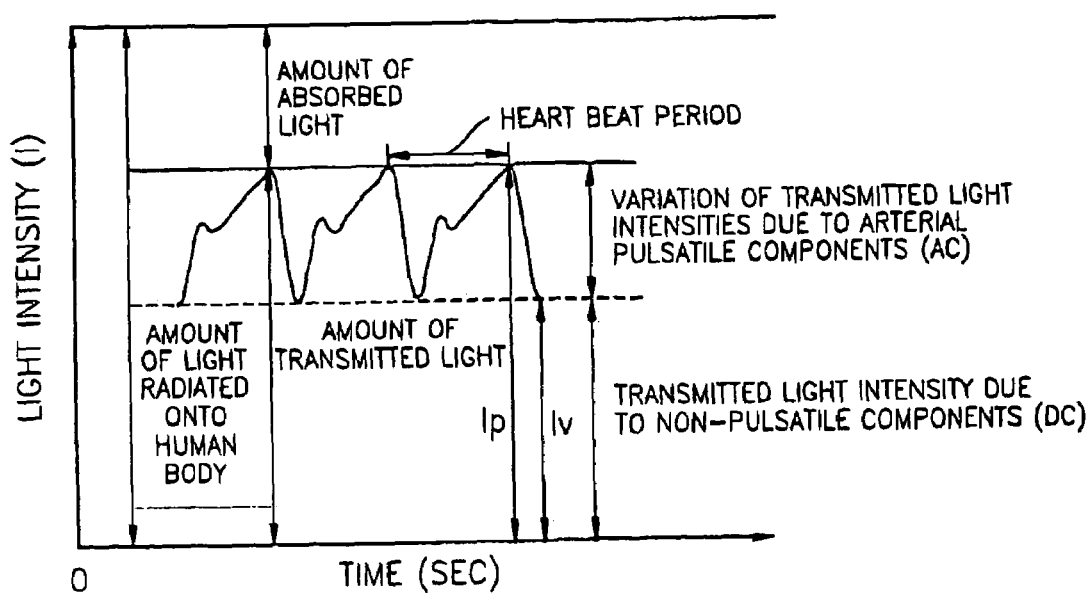
FIG. 13 is a conceptual diagram of a measured PPG waveform.

A method of measuring oxygen saturation according to the first embodiment of the present invention will now be described with reference to FIGS. 8, 9 and 13. Oxygen saturation is a percentage of a concentration of oxidized hemoglobin in a concentration of the total hemoglobin, i.e., a quantification of an amount of oxygen with which blood is saturated in order to maintain the normal functions of human cells. Many methods of detecting oxygen saturation using light having at least two different wavelengths have been researched and developed. In a representative method of measuring oxygen saturation among them, red light and infrared light are radiated onto vital tissue, absorbance of pulsatile components in the arterial blood is obtained at each wavelength, and oxygen saturation is calculated using a ratio between absorbances at different wavelengths. Most light radiated onto a human body is absorbed by non-pulsatile components such as bones and tissue having a constant transmission path, and about 1–2% of the light is absorbed by the pulsatile components in the arterial blood. The amount of light absorbed by the pulsatile components and the amount of light absorbed by the non-pulsatile components can be obtained at each wavelength using the intensities of the light transmitted through the human body. A ratio between an amount of light absorbed by the non-pulsatile components and an amount of light absorbed by the pulsatile components at each of the two different wavelengths of the red light and the infrared light, respectively, indicates a light absorptance of hemoglobin in the arterial blood. The oxygen saturation is calculated from a ratio between the amounts of light absorbed by hemoglobin at the two different wavelengths. In FIG. 13, "Ip" and "Iv" denote a maximum point and a minimum point, respectively, in a pulsatile component (alternating current).

Referring to FIG. 8, which shows the PPG measurement module 520 and the PPG signal processor 580, incident light from the first light source is transmitted through the body part. When the incident light passes through a path "a", it encounters a blood vessel, in this case, an artery, and is modulated by pulsation. When the incident light passes through a path "b", it is not influenced by pulsation. When a radius of the artery is "$r_a$" and a radius of the body part is "$r_b$", the entire time-invariant component DC of light detected by the photodetector is composed of a time-invariant component $DC_a$ of the light passing through the path "a" and a time-invariant component $DC_b$ of the light passing through the path "b", as shown in FIG. 13, and is expressed by Formula (4).

$$DC = DC_a + DC_b \quad (4)$$

$DC_a$ can be expressed by Formula (5).

$$DC_a = f(r_a, r_b, \lambda) DC \quad (5)$$

Here, $f(r_a, r_b, \lambda)$ is a constant denoting a factor changing according to the structure of the body part including an artery, and $\lambda$ denotes a wavelength of the incident light. An intensity of light transmitted through the body part is modulated by as much as a variation $\Delta OD_{tot}$ of light attenuation $OD_{tot}$ by a change in an amount of blood due to pulsation of the artery. Here, the variation $\Delta OD_{tot}$ is for the light passing through the path "a" and can be expressed by Formula (6).

$$\Delta OD_{tot} = AC/DC_a = f^{-1}(r_a, r_b, \lambda) AC/DC \quad (6)$$

Since it is very difficult to accurately measure $f(r_a, r_b, \lambda)$, reflection coefficients $R_1$ and $R_2$ for two wavelengths $\lambda 1$ and $\lambda 2$ are measured, and then a ratio $R_{12} = R_1/R_2$ is obtained, as shown in Formula (7), in order to calculate oxygen saturation without having to accurately measure $f(r_a, r_b, \lambda)$.

$$R_{12} = \frac{R_1}{R_2} = \frac{\Delta OD_{tot,\lambda 1}}{\Delta OD_{tot,\lambda 2}} = \frac{AC_{\lambda 1}/DC_{\lambda 1}}{AC_{\lambda 2}/DC_{\lambda 2}} \quad (7)$$

Here, $AC_{\lambda 1}$ and $AC_{\lambda 2}$ denote time-variant components with respect to the first and second wavelengths $\lambda 1$ and $\lambda 2$, and $DC_{\lambda 1}$ and $DC_{\lambda 2}$ denote time-invariant components with respect to the first and second wavelengths $\lambda 1$ and $\lambda 2$. For example, Formula (7) can be obtained using a pulse oximeter.

Consequently, as shown in Formula (7), the reflection coefficient detector (924 of FIG. 9) divides the time-variant component $AC_{\lambda 1}$ or $AC_{\lambda 2}$, which has been input from the photodetector through the peak detector 585 and detected by the AC detector 920, by the time-invariant component $DC_{\lambda 1}$ or $DC_{\lambda 2}$ detected by the DC detector 922 to obtain a variation $\Delta OD_{tot,\lambda 1}$ or $\Delta OD_{tot,\lambda 2}$ of light attenuation at each wavelength, and divides the variation $\Delta OD_{tot,\lambda 1}$ of attenuation of light from the first light source by the variation $\Delta OD_{tot,\lambda 2}$ of attenuation of light from the second light source to obtain a ratio of the reflection coefficient of the first light source to the reflection coefficient of the second light source.

The oxygen saturation detector 926 calculates a concentration $C_{Hb}$ of hemoglobin in blood using at least one ratio $R_{12}$ received from the reflection coefficient detector 924. According to an embodiment of the present invention, when the first and second wavelengths $\lambda 1$ and $\lambda 2$ are selected, the hemoglobin concentration $C_{Hb}$ is calculated using the ratio $R_{12}$, as shown in Formula (8).

$$C_{Hb} = \frac{35^2(\varepsilon_1 - R_{12}\varepsilon_2)}{k_1 a_1 - k_2 a_2 R_{12}} + 35 \quad (8)$$

Here, $\varepsilon_1$ denotes an absorption coefficient with respect to the first wavelength $\lambda 1$; $\varepsilon_2$ denotes an absorption coefficient with respect to the second wavelength $\lambda 2$; $k_1$ and $k_2$ denote constants determined by the first and second wavelengths $\lambda 1$ and $\lambda 2$ and characteristics of scattering and absorbing incident light at a predetermined body part; and $a_1$ and $a_2$ denote constants determined by a size of a scattered particle, a refractive index of hemoglobin, a refractive index of serum, and the first and second wavelengths $\lambda 1$ and $\lambda 2$.

The oxygen saturation detector 926 calculates oxygen saturation S using the measured hemoglobin concentration $C_{Hb}$, as shown in Formula (9), and outputs the oxygen saturation S to the display unit 590.

Hereinafter, a procedure in which the oxygen saturation detector 926 detects oxygen saturation will be described. One wavelength $\lambda x$ is selected from among at least two wavelengths, and another wavelength $\lambda o$ having a maximum difference in an absorption coefficient according to a type of hemoglobin is selected.

The wavelengths $\lambda x$ and $\lambda o$ are derived based on bio spectroscopy. While some wavelengths can or cannot be well absorbed according to an amount of hemoglobin (Hb) and oxy-hemoglobin ($HbO_2$) in blood, other wavelengths are well absorbed regardless of the amount of Hb and $HbO_2$. In the present invention, the reference wavelength $\lambda x$ is barely influenced by the amount of Hb and $HbO_2$, and the wavelength $\lambda o$ readily changes according to the amount of Hb and $HbO_2$. For example, the wavelength $\lambda o$ may be a wavelength of 660 nm giving a maximum difference between an absorption coefficient for Hb and an absorption coefficient for $HbO_2$, and the wavelength λx may be a wavelength of 805 nm selected from a near infrared band of 800 through 950 nm. A discussion of these characteristics of wavelengths may be found in a book by J. G. Webster entitled "Design of Pulse Oximeters," at pages 40–55, published in 1997.

The oxygen saturation detector 926 obtains a variation $\Delta OD_{tot,\lambda o}$ of light attenuation at the selected wavelength λo and a variation $\Delta OD_{tot,\lambda x}$ of light attenuation at the selected wavelength λx and obtains a ratio $R_{ox}$ of the variation $\Delta OD_{tot,\lambda o}$ to the variation $\Delta OD_{tot,\lambda x}$.

Thereafter, the oxygen saturation detector 926 calculates oxygen saturation S in blood using the ratio $R_{ox}$ and the hemoglobin concentration $C_{Hb}$ according to Formula (9).

$$S = \frac{R_{ox}(\varepsilon_{Hb,x} - \varepsilon_{Hb,o})C_{Hb} + (k_x a_x - k_o a_o)H(1-H)}{(\varepsilon_{HbO_2,o} - \varepsilon_{Hb,o})C_{Hb}} \quad (9)$$

Here, $\varepsilon_{HbO_2,o}$ denotes an absorption coefficient for $HbO_2$ with respect to the wavelength λo; $\varepsilon_{Hb,o}$ denotes an absorption coefficient for Hb with respect to the wavelength λo; $\varepsilon_{Hb,x}$ denotes an absorption coefficient for Hb with respect to the wavelength λx; $k_x$ and $k_o$ denote constants determined by the wavelengths λx and λo and characteristics of scattering and absorbing incident light at a predetermined body part; and $a_x$ and $a_o$ denote constants determined by a size of a scattered particle, a refractive index of hemoglobin, a refractive index of serum, and the wavelengths λx and λo.

Figure 14:
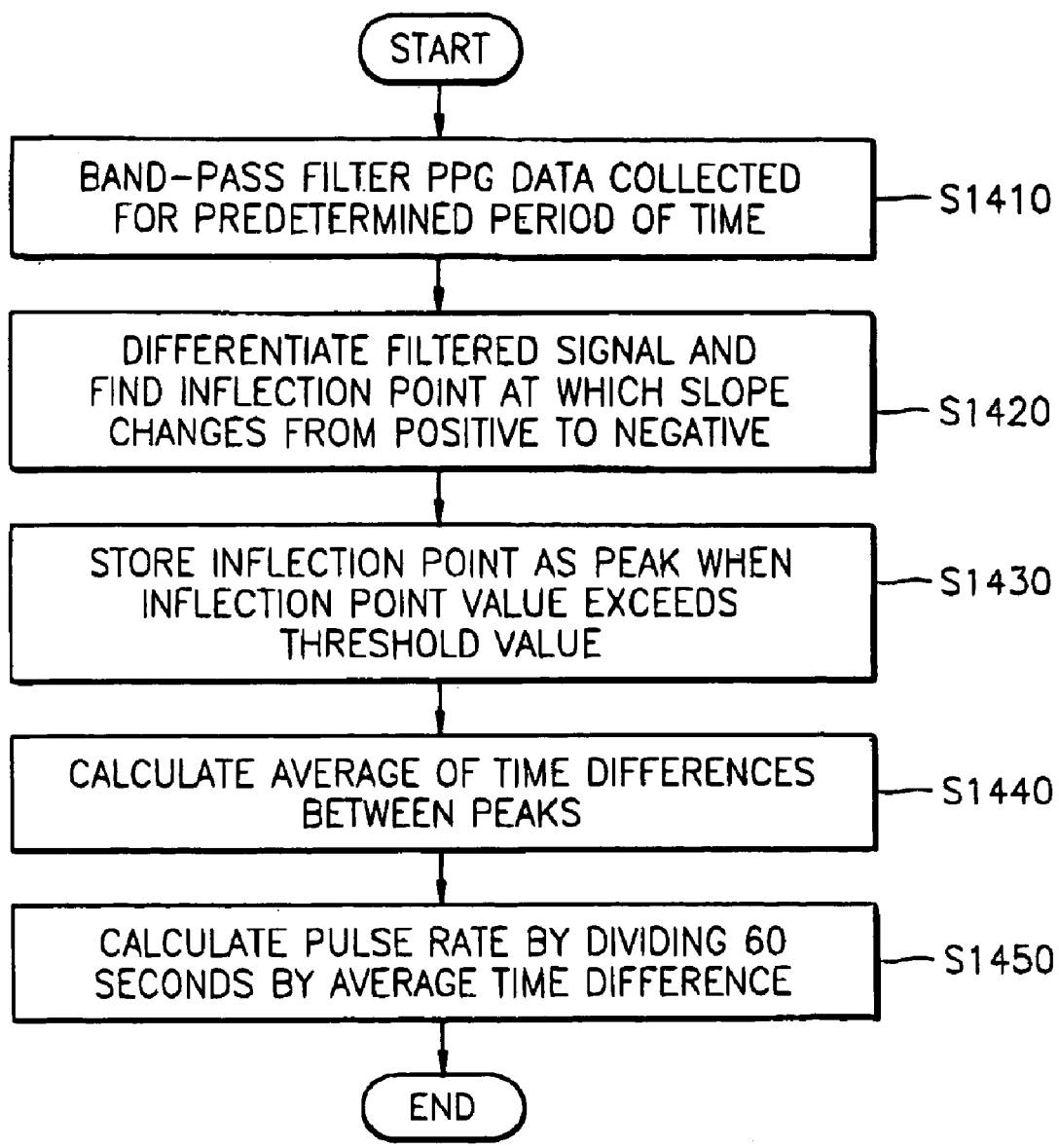
FIG. 14 is a flowchart of a method of measuring a pulse rate according to an embodiment of the present invention.

FIG. 14 is a flowchart of a method of measuring a pulse rate according to the first embodiment of the present invention. A method of measuring a pulse rate according to the first embodiment of the present invention will be described with further reference to FIGS. 9 and 14.

Figure 15A:
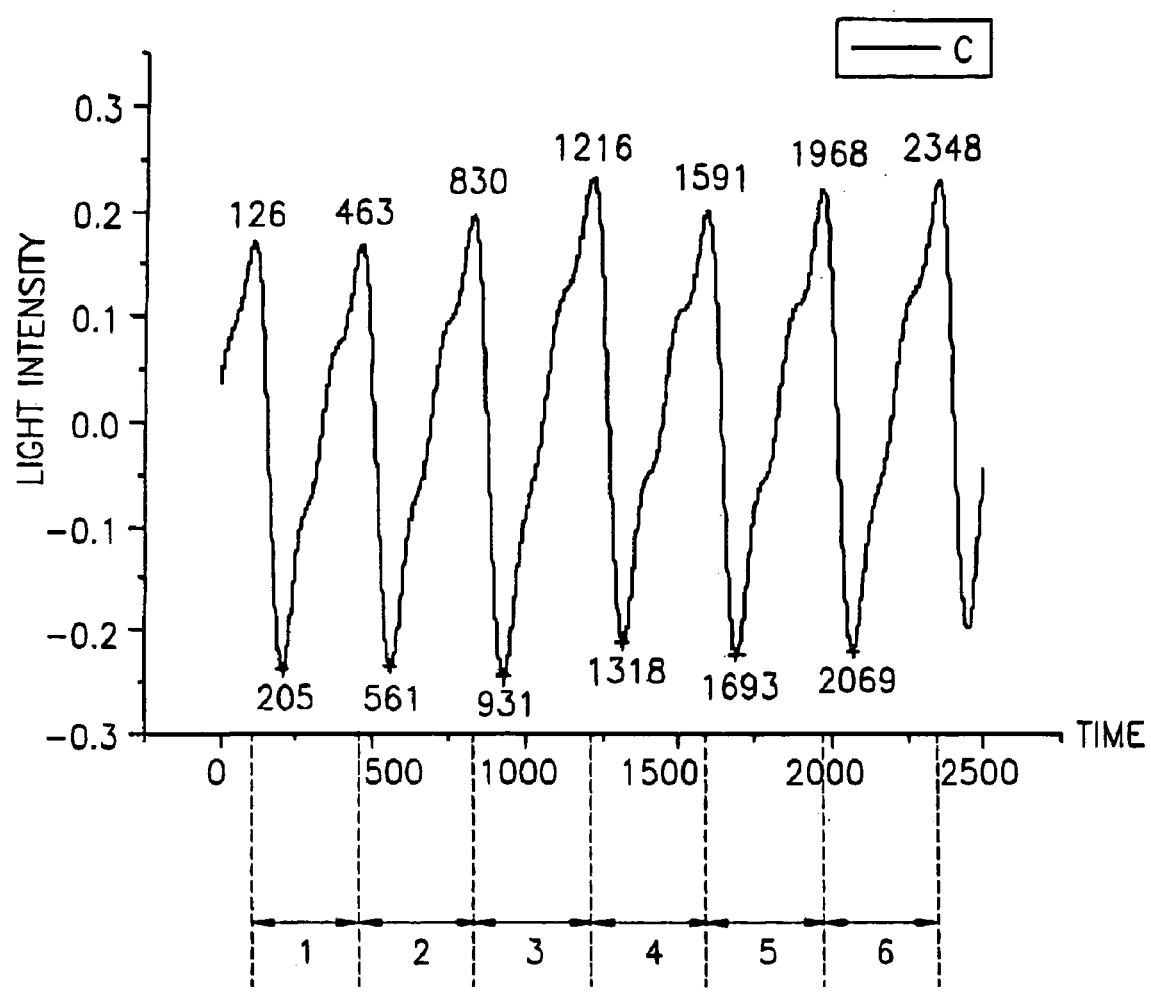
FIG. 15A is a diagram showing a detected pulse signal.

When a pulse wave necessary for performing a measurement of oxygen saturation is measured, a change in a blood flow rate in an artery is caused by a heart beat. A pulse rate is measured to measure the heart rate. As shown in FIG. 8, light transmitted through a predetermined body part is received and converted into an electrical signal by the photodetector. The electrical signal is amplified by the amplifier 581 and collected for a predetermined period of time, thereby forming PPG data. In step S1410, the PPG data is band pass filtered by the filter 583. In step S1420, the peak detector 585 differentiates the band-pass filtered signal and finds an inflection point at which a slope changes from positive to negative. In step S1430, an inflection point value is compared with a threshold value set initially, and the inflection point is detected as a peak when the inflection point value exceeds the threshold value, as shown in FIG. 15A. In step S1440, the pulse detector 910 calculates an average of time differences between peaks and, in step S1450, calculates a pulse rate per minute by dividing 60 seconds by the average time difference.

Figure 15B:
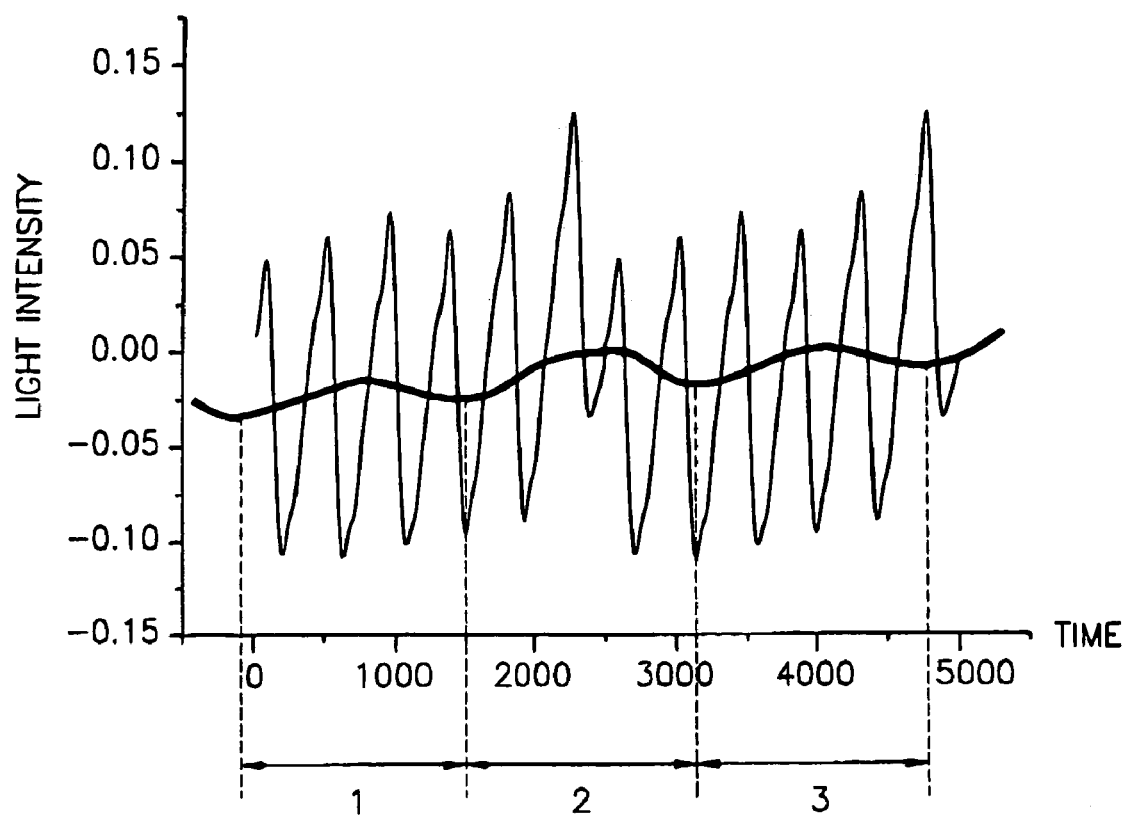
FIG. 15B illustrates a method of detecting respiration according to an embodiment of the present invention.

FIG. 15B illustrates a method of detecting a respiration frequency according to an embodiment of the present invention. Referring to FIGS. 9 and 15B, an AC component of a PPG is synchronized with a respiration signal as well as a heart beat. A PPG signal and respiration are related as follows. According to a mechanism based on maintenance of homeostasis of a human body, during inhalation, an intrathoracic pressure decreases, the amount of blood returning to the heart increases, a blood pressure increases due to an increase in a cardiac output, and a depressor center is excited to expand peripheral arteries. In contrast, during exhalation, the peripheral arteries are contracted. A change in an optical path length due to expansion and contraction of the peripheral arteries is reflected on the PPG. Synchronization between the AC component and the respiration signal occurs because a change in a blood flow rate is caused by respiration and reflected on the PPG.

In an embodiment of the present invention, frequency components in a respiration signal band are classified using a digital filter in order to extract a respiration signal from a PPG signal. A PPG signal output from the peak detector 585 is filtered by the BPF 930 having a cut-off frequency of about 0.13–0.48 Hz including a frequency band of a normal respiration signal. The respiration detector 935 detects a respiration signal from the filtered PPG signal, calculates an average respiration frequency by dividing 60 seconds by an average period of the respiration signal, and outputs the average respiration frequency to the display unit 590.

Figure 16A:
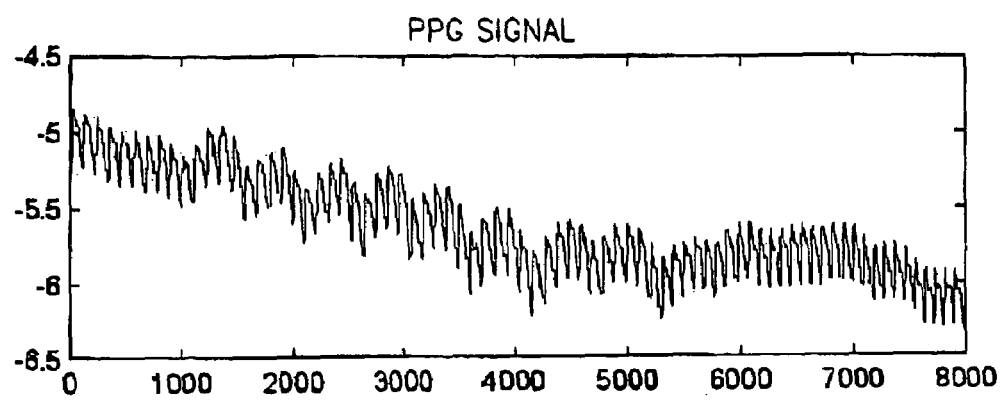
FIGS. 16A and 16B show a PPG signal and a respiration signal, respectively, which are simultaneously measured.
Figure 16B:
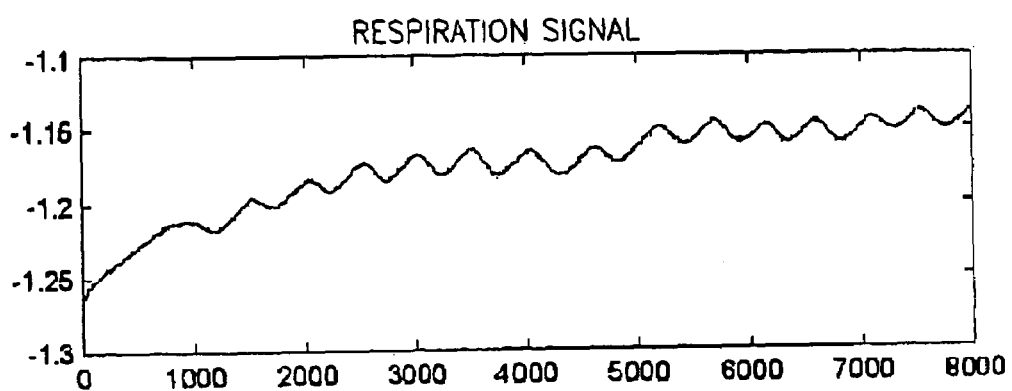
Figure 17A:
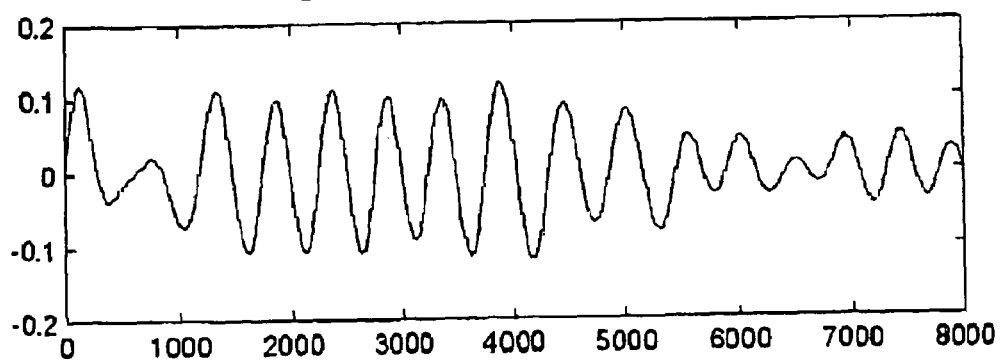
FIGS. 17A and 17B, respectively, show a respiration signal detected using a PPG signal and a respiration signal obtained by high-pass filtering the respiration signal shown in FIG. 16B.
Figure 17B:
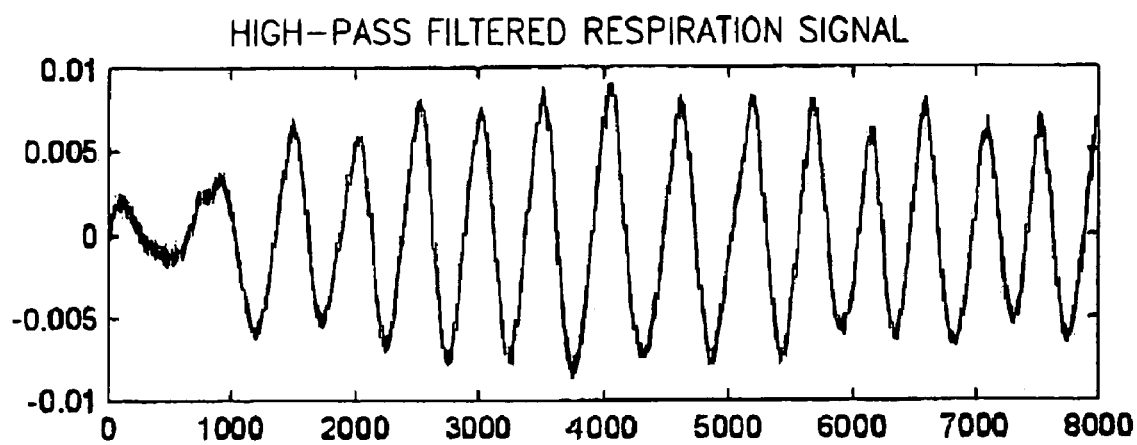

FIGS. 16A and 16B show a PPG signal and a respiration signal, respectively, measured to verify the present invention. FIG. 17A shows a PPG waveform obtained by band-pass filtering the PPG signal shown in FIG. 16A. FIG. 17B shows a waveform obtained by removing low-frequency components from the respiration signal shown in FIG. 16B. It may be seen from a comparison of FIGS. 17A and 17B that the band-pass filtered PPG signal closely correlates with the respiration signal.

Figure 18:
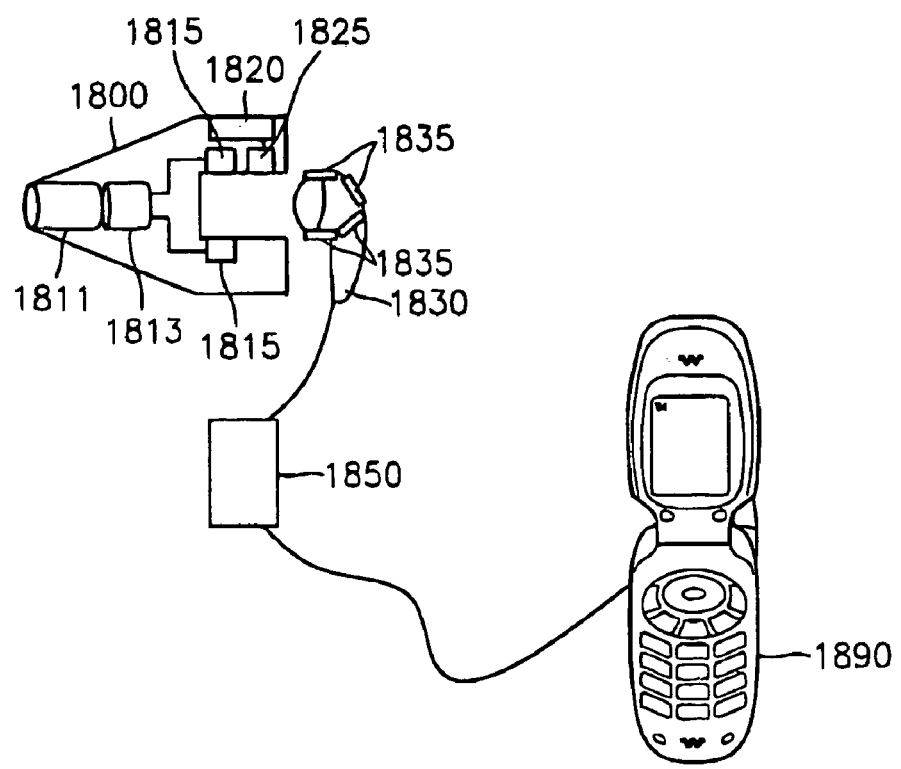
FIG. 18 illustrates a schematic diagram of an apparatus for measuring a bio signal according to a second embodiment of the present invention.

FIG. 18 is a block diagram of an apparatus for measuring a bio signal according to a second embodiment of the present invention. Referring to FIG. 18, the second embodiment is different from the first embodiment in that a bio signal measurement unit 1800 has a cap shape so that it may be mounted on an earphone 1830 reproducing voice from an existing portable apparatus when a bio signal is measured. The bio signal measurement unit 1800, a controller 1850, and a display unit 1890 have the same structures as those described in connection with the first embodiment, and thus only the difference between the first and second embodiments will be described.

In the second embodiment, the earphone 1830 supplies driving power to a temperature measurement module including a waveguide 1811 and an infrared sensor 1813 and to a PPG measurement module 1820 and has a plurality of electrodes 1835 on an outer surface for receiving a measured signal. The bio signal measurement unit 1800 has a recess into which the earphone 1830 is inserted. A plurality of electrodes 1815 and 1825 are disposed in the recess so that they are connected to the electrodes 1835 of the earphone 1830 when the earphone 1830 is inserted into the recess. The waveguide 1811 collecting infrared rays and the infrared sensor 1813 converting the collected infrared rays to an electrical signal are installed within the cap shape of the bio signal measurement unit 1800.

When measuring a bio signal, a user mounts the cap-shaped bio signal measurement unit 1800 on the earphone 1830 such that the electrodes 1815 and 1825 are connected to the electrodes 1835 and then inserts the bio signal measurement unit 1800 combined with the earphone 1830 into his ear.

The present invention may be realized as a code that is recorded on a computer readable recording medium and can be read by a computer. The computer readable recording medium may be any type of medium on which data that can be read by a computer system can be recorded, for example, a ROM, a RAM, a CD-ROM, a magnetic tape, a floppy disc, or an optical data storage device. The present invention may also be realized as carrier waves (for example, transmitted through Internet). Alternatively, computer readable recording media may be distributed among computer systems connected through a network so that the present invention can be realized as a code that is stored in the recording media and can be read and executed in the computers.

As described above, an apparatus for measuring a bio signal according to an embodiment of the present invention includes a module measuring various types of bio information and is structured to be insertable into the ear so that various types of bio information can be simultaneously measured and an influence of a motion artifact can be minimized. In addition, an error occurring due to contamination or damage of a sensor can be reduced.

Moreover, since an apparatus for measuring a bio signal according to an embodiment of the present invention can be connected to a mobile apparatus such as an earphone, it is convenient to carry. Further, a user is able to reposition the mount of the apparatus based on feel while observing a measured value displayed on a mobile apparatus. Thus, the user is bale to perform measurements on himself and self-diagnose a condition.

When an apparatus for measuring a bio signal according to an embodiment of the present invention is combined with a mobile communication terminal, a measured bio signal can be displayed to a user through a display apparatus included in the mobile communication terminal and easily transmitted to a remote medical institution through the mobile communication terminal. As a result, remote medical treatment is possible.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. An apparatus for measuring a bio signal, comprising:
   a bio signal measurement unit, which is insertable into an ear to be in close contact with an internal surface of the ear, the bio signal measurement unit having a photoplethysmography (PPG) measurement module for radiating light of different wavelengths onto the internal surface of the ear, detecting light transmitted through the ear, and outputting a PPG signal including bio information;
   a control unit having a PPG signal processor for generating the bio information using the PPG signal measured by the PPG measurement module and a sound processor for simultaneously outputting a sound signal without any bio information signal interference, wherein the control unit outputs the bio information when a signal received by the control unit corresponds to the bio information, and outputs the sound signal when a signal received by the control unit corresponds to the sound signal;
   an output unit for displaying the bio information generated from the control unit; and
   an earphone connected to the control unit for outputting the sound signal received from the control unit, wherein the control unit further includes a sound processor for controlling the volume of the sound signal.

2. The apparatus as claimed in claim 1, wherein the PPG measurement module comprises:
   a light source unit for radiating light onto the internal surface of the ear; and
   a photodetector for detecting light radiated onto the internal surface of the ear and then transmitted through the ear.

3. The apparatus as claimed in claim 2, wherein the light source unit comprises:
   a first light source for radiating light of a first wavelength onto the internal surface of the ear; and
   a second light source for radiating light of a second wavelength onto the internal surface of the ear,
   wherein the first and second wavelengths are different.

4. The apparatus as claimed in claim 1, wherein the PPG signal processor comprises:
   a peak detector for detecting peaks of the PPG signal; and
   a signal processor for generating the bio information using values of the peaks.

5. The apparatus as claimed in claim 4, wherein the signal processor comprises a pulse detector for calculating a time interval between the peaks to measure a pulse rate.

6. The apparatus as claimed in claim 4, wherein the signal processor comprises a respiration detector for band-pass filtering the PPG signal to measure a respiration frequency.

7. The apparatus as claimed in claim 4, wherein the signal processor comprises:
   a reflection coefficient detector for detecting an AC component and a DC component from each of PPG signals detected at different wavelengths and measuring reflection coefficients; and
   an oxygen saturation detector for detecting oxygen saturation in blood using a ratio between the reflection coefficients of the different wavelengths.

8. The apparatus as claimed in claim 4, wherein the PPG signal processor further comprises:
   an amplifier for amplifying the PPG signal; and
   a filter for removing noise components from the PPG signal amplified by the amplifier and then outputting the PPG signal to the peak detector.

9. The apparatus as claimed in claim 1, wherein the bio signal measurement unit further comprises a temperature measurement module for sensing infrared rays radiated from a body and outputting an electrical signal corresponding to the sensed infrared rays, and wherein the control unit further includes a temperature processor for calculating a body temperature using the electrical signal output from the temperature measurement module.

10. The apparatus as claimed in claim 9, wherein the temperature measurement module comprises:
    a waveguide configured to be installed near an eardrum for guiding infrared rays radiated from the eardrum; and
    a light receiver for sensing the infrared rays guided by the waveguide and converting the infrared rays to the electrical signal.

11. The apparatus as claimed in claim 10, wherein the waveguide is made of a material that can reflect infrared rays.

12. The apparatus as claimed in claim 9, wherein the temperature processor comprises:
    an amplifier for amplifying the electrical signal received from the temperature measurement module;
    a filter for removing noise from the amplified electrical signal; and
    an analog-to-digital converter for converting the electrical signal to a digital signal.

13. The apparatus as claimed in claim 9, wherein the output unit is a liquid crystal display apparatus.

14. The apparatus as claimed in claim 9, wherein the output unit is a liquid crystal display apparatus of a mobile communication terminal.

15. The apparatus as claimed in claim 9, further comprising a mobile communication terminal through which the bio information generated from the control unit is wirelessly transmitted to a predetermined medical institution.

16. The apparatus as claimed in claim 9, wherein the output unit is a liquid crystal display apparatus of a compact disc player.

17. The apparatus as claimed in claim 1, wherein the output unit is a liquid crystal display apparatus.

18. The apparatus as claimed in claim 1, wherein the output unit is a liquid crystal display apparatus of a mobile communication terminal.

19. The apparatus as claimed in claim 1, further comprising a mobile communication terminal through which the bio information generated from the control unit is wirelessly transmitted to a predetermined medical institution.

20. The apparatus as claimed in claim 1, wherein the output unit is a liquid crystal display apparatus of a compact disc player.

21. The apparatus as claimed in claim 1, wherein the sound processor for controlling the volume of the sound signal outputs the sound signal to the earphone having a speaker.

22. An apparatus for measuring a bio signal, comprising:
a bio signal measurement unit, which is insertable into an ear to be in close contact with an internal surface of the ear, the bio signal measurement unit having a photo plethysmography (PPG) measurement module for radiating light of different wavelengths onto the internal surface of the ear, detecting light transmitted through the ear, and outputting a PPG signal including bio information, and further having a first plurality of electrodes for outputting the PPG signal;
an earphone having a speaker for outputting sound a second plurality of electrodes on an outer surface to be connected to the first plurality of electrodes of the bio signal measurement unit to receive the PPG signal output from the bio signal measurement unit;
a control unit having a PPG signal processor for receiving the PPG signal through the electrodes of the earphone and generating bio information using the PPG signal and a sound processor for simultaneously outputting a sound signal without any bio information signal interference to the earphone; and
an output unit for displaying the bio information generated from the control unit.

23. The apparatus as claimed in claim 22, wherein the PPG measurement module comprises:
a light source unit for radiating light onto the internal surface of the ear; and
a photodetector for detecting light radiated onto the internal surface of the ear and then transmitted through the ear.

24. The apparatus as claimed in claim 23, wherein the light source unit comprises:
a first light source for radiating light of a first wavelength onto the internal surface of the ear; and
a second light source for radiating light of a second wavelength onto the internal surface of the ear, and
wherein the first and second wavelengths are different.

25. The apparatus as claimed in claim 22, wherein the PPG signal processor comprises:
a peak detector for detecting peaks of the PPG signal; and
a signal processor for generating the bio information using values of the peaks.

26. The apparatus as claimed in claim 25, wherein the signal processor comprises a pulse detector for calculating a time interval between the peaks to measure a pulse rate.

27. The apparatus as claimed in claim 25, wherein the signal processor comprises a respiration detector for bandpass filtering the PPG signal to measure a respiration frequency.

28. The apparatus as claimed in claim 25, wherein the signal processor comprises:
a reflection coefficient detector for detecting an AC component and a DC component from each of PPG signals detected at different wavelengths and measuring reflection coefficients; and
an oxygen saturation detector for detecting oxygen saturation in blood using a ratio between the reflection coefficients of the different wavelengths.

29. The apparatus as claimed in claim 25, wherein the PPG signal processor further comprises:
an amplifier for amplifying the PPG signal; and
a filter for removing noise components from the PPG signal amplified by the amplifier and then outputting the PPG signal to the peak detector.

30. The apparatus as claimed in claim 22, wherein the bio signal measurement unit further comprises a temperature measurement module for sensing infrared rays radiated from a body and outputting an electrical signal corresponding to the sensed infrared rays, and wherein the control unit further includes a temperature processor for calculating a body temperature using the electrical signal output from the temperature measurement module.

31. The apparatus as claimed in claim 30, wherein the temperature measurement module comprises:
a waveguide configured to be installed near an eardrum for guiding infrared rays radiated from the eardrum; and
a light receiver for sensing the infrared rays guided by the waveguide and converting the infrared rays to the electrical signal.

32. The apparatus as claimed in claim 31, wherein the waveguide is made of a material that can reflect infrared rays.

33. The apparatus as claimed in claim 30, wherein the temperature processor comprises:
an amplifier for amplifying the electrical signal received from the temperature measurement module;
a filter for removing noise from the amplified electrical signal; and
an analog-to-digital converter for converting the electrical signal to a digital signal.

34. The apparatus as claimed in claim 30, wherein the output unit is a liquid crystal display apparatus.

35. The apparatus as claimed in claim 30, wherein the output unit is a liquid crystal display apparatus of a mobile communication terminal.

36. The apparatus as claimed in claim 30, further comprising a mobile communication terminal through which the bio information generated from the control unit is wirelessly transmitted to a predetermined medical institution.

37. The apparatus as claimed in claim 30, wherein the output unit is a liquid crystal display apparatus of a compact disc player.

38. The apparatus as claimed in claim 22, wherein the output unit is a liquid crystal display apparatus.

39. The apparatus as claimed in claim 22, wherein the output unit is a liquid crystal display apparatus of a mobile communication terminal.

40. The apparatus as claimed in claim 22, further comprising a mobile communication terminal through which the bio information generated from the control unit is wirelessly transmitted to a predetermined medical institution.

41. The apparatus as claimed in claim 22, wherein the output unit is a liquid crystal display apparatus of a compact disc player.

42. A method of measuring a bio signal using an ear type bio signal measurement apparatus including a bio signal measurement unit, which is insertable into an ear to measure a bio signal, an earphone having a speaker for outputting a sound signal, a control unit for generating bio information using the measured bio signal and for simultaneously providing the sound signal to the earphone without any bio information signal interference, and an output unit for outputting the bio information, the method comprising:
- (a) receiving infrared rays radiated from an eardrum and measuring a body temperature using the bio signal measurement unit to be provided as a bio signal;
- (b) radiating light having different wavelengths onto an internal surface of an ear, which is in close contact with the bio signal measurement unit, to measure a photo plethysmography (PPG) signal including bio information and measuring at least one bio signal from among the group consisting of oxygen saturation, a pulse rate, and a respiration frequency, using the PPG signal; and
- (c) outputting the at least one bio signal measured in (a) and (b) to the output unit when a signal received by the control unit corresponds to the bio signal and outputting the sound signal to the earphone when a signal received by the control unit corresponds to the sound signal, wherein (a) and (b) are simultaneously performed.

43. The method as claimed in claim 42, wherein (b) comprises:
- (b1) radiating the light having the different wavelengths onto the internal surface of the ear, receiving the light transmitted through the ear, and outputting the PPG signal, using a PPG measurement module included in the bio signal measurement unit having a side thereof in close contact with the internal surface of the ear;
- (b2) detecting peaks of the PPG signal; and
- (b3) generating bio information using the detected peaks.

44. The method as claimed in claim 43, wherein (b3) comprises:
- detecting an AC component and a DC component from each of PPG signals detected at the different wavelengths and measuring reflection coefficients of the different wavelengths; and
- calculating oxygen saturation in blood using a ratio between the reflection coefficients of the different wavelengths.

45. The method as claimed in claim 43, wherein (b3) comprises band-pass filtering the PPG signal to detect a respiration frequency.

46. The method as claimed in claim 43, wherein (b2) comprises:
- band-pass filtering the PPG signal collected for a predetermined period of time;
- detecting an inflection point by differentiating the filtered PPG signal; and
- storing the inflection point as a peak when the inflection point has a value exceeding a predetermined threshold value.

47. The method as claimed in claim 43, wherein (b3) comprises measuring a pulse rate using a time interval between peaks of the PPG signal.

48. The method as claimed in claim 42, wherein the output unit is a liquid crystal display apparatus of a mobile communication terminal, and (c) further includes wirelessly transmitting the bio signals measured in (a) and (b) to a predetermined medical institution through the mobile communication terminal.

49. A recording medium having recorded therein a program for executing the method of claim 42 in a computer.

\* \* \* \* \*